(12) United States Patent
Zheng et al.

(10) Patent No.: US 10,413,580 B2
(45) Date of Patent: Sep. 17, 2019

(54) COMPOSITIONS COMPRISING *CYCLOCARYA PALIURUS* EXTRACT AND PREPARATION METHOD AND USES THEREOF

(71) Applicant: Infinitus (China) Company LTD, Jiang Men, Guangdong (CN)

(72) Inventors: Xia Zheng, Guangzhou (CN); Xiaolei Guo, Guangzhou (CN); Chung Wah Ma, Guangzhou (CN); Zhen Luo, Guangzhou (CN)

(73) Assignee: INFINITUS (CHINA) COMPANY LTD, Jiangmen (CN)

( * ) Notice: Subject to any disclaimer, the term of this patent is extended or adjusted under 35 U.S.C. 154(b) by 0 days.

(21) Appl. No.: 15/128,827

(22) PCT Filed: Apr. 28, 2016

(86) PCT No.: PCT/CN2016/080547
§ 371 (c)(1),
(2) Date: Sep. 23, 2016

(87) PCT Pub. No.: WO2016/173509
PCT Pub. Date: Nov. 3, 2016

(65) Prior Publication Data
US 2017/0202897 A1 Jul. 20, 2017

(30) Foreign Application Priority Data

Apr. 29, 2015 (CN) .......................... 2015 1 0212607
Apr. 29, 2015 (CN) .......................... 2015 1 0213059
Apr. 29, 2015 (CN) .......................... 2015 1 0214436

(51) Int. Cl.
| | |
|---|---|
| *A61K 36/82* | (2006.01) |
| *A61K 36/752* | (2006.01) |
| *A61K 36/8984* | (2006.01) |
| *A61K 36/52* | (2006.01) |
| *A61K 36/605* | (2006.01) |
| *A61K 9/16* | (2006.01) |
| *A61K 9/48* | (2006.01) |
| *A23L 33/00* | (2016.01) |
| *A47G 19/16* | (2006.01) |
| *B65D 85/808* | (2006.01) |
| *A61K 36/488* | (2006.01) |
| *A61K 36/88* | (2006.01) |
| *A61K 36/8969* | (2006.01) |
| *A61K 36/185* | (2006.01) |
| *A61K 36/42* | (2006.01) |
| *A61P 3/06* | (2006.01) |
| *A61P 9/12* | (2006.01) |
| *A61P 3/10* | (2006.01) |

(52) U.S. Cl.
CPC .............. *A61K 36/82* (2013.01); *A23L 33/40* (2016.08); *A47G 19/16* (2013.01); *A61K 9/16* (2013.01); *A61K 9/1623* (2013.01); *A61K 9/1652* (2013.01); *A61K 9/485* (2013.01); *A61K 9/4808* (2013.01); *A61K 9/4825* (2013.01); *A61K 9/4833* (2013.01); *A61K 9/4866* (2013.01); *A61K 36/185* (2013.01); *A61K 36/42* (2013.01); *A61K 36/488* (2013.01); *A61K 36/52* (2013.01); *A61K 36/605* (2013.01); *A61K 36/752* (2013.01); *A61K 36/88* (2013.01); *A61K 36/8969* (2013.01); *A61K 36/8984* (2013.01); *A61P 3/06* (2018.01); *A61P 3/10* (2018.01); *A61P 9/12* (2018.01); *B65D 85/808* (2013.01); *A23V 2002/00* (2013.01); *A61K 2236/00* (2013.01); *A61K 2236/13* (2013.01); *A61K 2236/15* (2013.01); *A61K 2236/17* (2013.01); *A61K 2236/51* (2013.01); *H05K 999/99* (2013.01)

(58) Field of Classification Search
None
See application file for complete search history.

(56) References Cited

U.S. PATENT DOCUMENTS

| | | | |
|---|---|---|---|
| 2005/0048137 A1* | 3/2005 | Wu | ..................... A61K 36/8984 424/725 |
| 2009/0004281 A1* | 1/2009 | Nghiem | ............... A61K 9/0004 424/490 |
| 2011/0027305 A1 | 2/2011 | Lee | |
| 2017/0173101 A1 | 6/2017 | Zhen et al. | |
| 2017/0173103 A1 | 6/2017 | Wah et al. | |

FOREIGN PATENT DOCUMENTS

| | | | |
|---|---|---|---|
| CN | 1389146 A | | 1/2003 |
| CN | 101028363 | * | 9/2007 |
| CN | 101433332 A | | 5/2009 |

(Continued)

OTHER PUBLICATIONS

Kim et al. Acta Pharm Res V 22, No. 1, pp. 9-12. publication year: 1999.*

(Continued)

*Primary Examiner* — Terry A McKelvey
*Assistant Examiner* — Catheryne Chen
(74) *Attorney, Agent, or Firm* — Morrison & Foerster LLP

(57) ABSTRACT

Compositions and preparation method thereof, said compositions comprise an extract from a mixture comprising *Cyclocarya paliurus* leaves and one or more herbs selected from the group consisting of *Mori Cortex, Dendrobii Caulis* and *Citri Reticulatae Pericarpium*, said compositions can treat diabetes, hyperglycemia, hypertension and/or hyperlipidemia.

17 Claims, 11 Drawing Sheets

(56) References Cited

FOREIGN PATENT DOCUMENTS

| CN | 101744888 A | * | 6/2010 |
|---|---|---|---|
| CN | 101744888 A | | 6/2010 |
| CN | 101879278 A | | 11/2010 |
| CN | 101979639 A | | 2/2011 |
| CN | 102000168 A | | 4/2011 |
| CN | 102048958 A | * | 5/2011 |
| CN | 102552388 A | | 7/2012 |
| CN | 102754710 A | | 10/2012 |
| CN | 102525945 B | | 5/2013 |
| CN | 103893620 A | | 7/2014 |
| CN | 103920151 A | | 7/2014 |
| CN | 103989980 A | | 8/2014 |
| CN | 104069370 A | | 10/2014 |
| CN | 104187361 A | | 12/2014 |
| CN | 104189744 A | * | 12/2014 |
| CN | 104784258 A | | 7/2015 |
| CN | 104839662 A | | 8/2015 |
| CN | 104855974 A | | 8/2015 |
| CN | 104996993 A | | 10/2015 |
| WO | WO-2015/003324 A1 | | 1/2015 |
| WO | WO-2016/173509 A1 | | 11/2016 |
| WO | WO-2016/173511 A1 | | 11/2016 |
| WO | WO-2016/173512 A1 | | 11/2016 |

OTHER PUBLICATIONS

Google Patents. Machine Translation of Shu CN 101028363 [online]. Publication date: Sep. 5, 2005 [retrieved on Jun. 17, 2017]. Retrieved from the internet: <https://www.google.com/patents/CN101028363A?cl=en&dq=cn+101028363&hl=en&sa=X&ved=0ahUKEwij5cuDr8XUAhWMWD4KHXyKAHkQ6AEIJDAA>.*

Li-Hua, C. et al. (Dec. 31, 2005). "The Distributing of Natural Hypoglycemic Functional Factors," *Modern Food Science and Technology* 21(3):172-175, (English Abstract only).

Sen, M.A. (Apr. 30, 2010). "Studies on Reducing Blood Sugar Effect of Citrus Peel and Dried Tangerine Peel," *Journal of Wuyi College* 29(2):18-20, (English Abstract only).

Zhou, W. et.al (Apr. 30, 2013). "Progress of Effective Ingredients of Traditional Chinese Medicine on Diabetes Therapy," *Journal of Guangdong Pharmaceutical University* 29(2):219-222, (English Abstract only).

International Search Report dated Jul. 15, 2016, for PCT Application No. PCT/CN2016/080547 filed on Apr. 28, 2016, six pages.
International Search Report dated Jul. 15, 2016, for PCT Application No. PCT/CN2016/080553 filed on Apr. 28, 2016, six pages.
International Search Report dated Jul. 22, 2016, for PCT Application No. PCT/CN2016/080551, filed Apr. 28, 2016, six pages.
Written Opinion of the International Searching Authority dated Jul. 15, 2016, for PCT Application No. PCT/CN2016/080547 filed on Apr. 28, 2016, five pages.
Written Opinion of the International Searching Authority dated Jul. 22, 2016, for PCT Application No. PCT/CN2016/080551 filed on Apr. 28, 2016, seven pages.
Written Opinion of the International Searching Authority dated Jul. 15, 2016, for PCT Application No. PCT/CN2016/080553 filed on Apr. 28, 2016, seven pages.
Abou-Seif, M.A.M. et al. (2008). "Hypoglycemic and Metabolic Activity of Aqueous Extract of *Morus alba* in Streptozotocin-Diabetic Rats," *Bioscience, Biotechnology Research Asia* 5(1):139-144. English Replacement Paper for reference: Abou-Seif, M.A.M. et al. (Jun. 1, 2009). "Hypoglycemic and Metabolic Activity of Aqueous Extract of Morus Alba in Streptozotocin-Diabetic Rats," *Medicinal & Aromatic Plants Abstracts* 31(3).
Shu, X.-S. et al. (Jul. 30, 2009; e-published on May 18, 2009). "Antihyperglycemic Effects of Total Flavonoids from *Polygonatum Odoratum* in STZ and Alloxan-Induced Diabetic Rats," Journal of *Ethnopharmacology* 124(3):539-543.
Son, Hee-Kyoung et al. (Aug. 30, 2014). "Anti-Diabetic Effect of the Mixture of Mulberry Leaf and Green Tea Powder in Rats with Streptozotocin-Induced Diabetes," *Korean Journal of Food Preservation* 21(4):549-559, (English Abstract only).
Wang, Qingqing et al. (2013; e-published on Oct. 30, 2013). "Antihyperglycemic, Antihyperlipidemic and Antioxidant Effects of Ethanol and Aqueous Extracts of *Cyclocarya paliurus* leaves in Type 2 Diabetic Rats," *Journal of Ethnopharmacology* 150(3):1119-1127.
European Search Report dated Dec. 7, 2017 for EP Application No. 16785075.9, thirteen pages.
European Search Report dated Dec. 7, 2017 for EP Application No. 16785076.7, eleven pages.
European Search Report dated Mar. 12, 2018 for EP Application No. 16785077.5, nine pages.

* cited by examiner

| Chinese Herbal Medicine | Chinese Name | Chinese Herbal Medicine | Chinese Name |
|---|---|---|---|
| Aloe | 芦荟 | *Ligustri lucidi Fructus* | 女贞子 |
| *Anemarrhenae Rhizoma* | 知母 | *Longan* leaves | 龙眼叶 |
| *Angelicae sinensis Radix* | 当归 | *Lycii Fructus* | 枸杞子 |
| *Astragali Radix* | 黄芪 | *Lycii Folium* | 枸杞叶 |
| *Atractylodis Rhizoma* | 苍术 | *Mori Cortex* | 桑白皮 |
| Balsam pear | 苦瓜 | *Mori Folium* | 桑叶 |
| Black Tea | 红茶 | *Mume Fructus* | 乌梅 |
| *Broadleaf Holly* leaf | 苦丁茶 | *Myrica rubra* leaves | 杨梅叶 |
| Buckwheat leaves | 荞麦叶 | *Notoginseng Radix et Rhizoma* | 三七 |
| Celery | 芹菜 | *Ophiopogonis Radix* | 麦门冬 |
| *Chuanxiong Rhizoma* | 川芎 | *Paeoniae Radix alba* | 白芍 |
| *Citri Reticulatae Pericarpium* | 陈皮 | *Panacis Quinquefolii Radix* | 西洋参 |
| *Corn Stigma* | 玉米须 | *Polygonati odorati Rhizoma* | 玉竹 |
| *Corni Fructus* | 山茱萸 | *Polygonati Rhizoma* | 黄精 |
| *Cyclocarya paliurus* leaves | 青钱柳叶 | *Poria* | 茯苓 |
| *Dendrobii Caulis* | 石斛 | Prepared Rhubarb | 制大黄 |
| *Dioscoreae Rhizoma* | 山药 | *Puerariae lobatae Radix* | 葛根 |
| *Eriobotryae Folium* | 枇杷叶 | Pumpkin | 南瓜 |
| *Fagopyrum tataricum* | 苦荞麦 | *Rehmanniae Radix* | 生地黄 |
| Garlic | 大蒜 | *Rhodiolae Crenulatae Radix et Rhizoma* | 红景天 |
| *Ginkgo Folium* | 银杏叶 | *Schisandrae chinensis Fructus* | 五味子 |
| *Ginseng Radix et Rhizoma* | 人参 | *Scrophulariae Radix* | 玄参 |
| Green Tea | 绿茶 | *Siraitiae Fructus* | 罗汉果 |
| *Gynostemma pentaphyllum* | 绞股蓝 | Sweet Potato leaves | 番薯叶 |
| *Hericium erinaceus* | 猴头菇 | *Tremella* | 银耳 |
| Konjac | 魔芋 | *Tribuli Fructus* | 蒺藜 |
| *Laminariae Thallus/Eckloniae Thallus* | 昆布 | | |

FIG. 11

COMPOSITIONS COMPRISING *CYCLOCARYA PALIURUS* EXTRACT AND PREPARATION METHOD AND USES THEREOF

CROSS-REFERENCE TO RELATED APPLICATIONS

This application is a National Phase application under 35 U.S.C. § 371 of International Application No. PCT/CN2016/080547 filed Apr. 28, 2016, which claims priority to People's Republic of China Patent Application No. 201510212607.0 filed Apr. 29, 2015, People's Republic of China Patent Application No. 201510214436.5 filed Apr. 29, 2015, and People's Republic of China Patent Application No. 201510213059.3 filed Apr. 29, 2015, the disclosures of each of which are hereby incorporated herein by reference in their entireties.

FIELD OF THE INVENTION

The present invention relates to the field of herbal medicine and herbal nutritional composition. In particular, the present invention relates to processed herbal compositions (such as an extract) comprising *Cyclocarya paliurus* leaves and other herbs (such as *Mori Cortex, Dendrobii Caulis* and *Citri Reticulatae Pericarpium*), and their use in lowering blood sugar and treating hyperglycemia, hypertension and/or hyperlipidemia.

BACKGROUND

Diabetes mellitus is a chronic metabolic disease characterized by high levels of blood sugar in afflicted individuals. Long-term elevated sugar levels in the blood can lead to serious damage to many parts of the body, including blood vessels, kidney, and the nervous system. Because of rapid economic growth and urbanization, an increasing population of the world adopts a high-carbohydrate diet and a sedentary life style, which are major factors contributing to a global epidemic of diabetes. According to the World Health Organization, more than 347 million people worldwide live with diabetes, and an estimated 1.5 million deaths were directly caused by diabetes in 2012 alone. A safe and effective method for long-term management of blood sugar levels is therefore in urgent need.

Currently, the most widely used antidiabetic therapies include insulin, insulin stimulators, and insulin sensitizers, all of which act on insulin, a peptide hormone, or its interacting partners in the insulin signaling pathway that regulates sugar metabolism in the body. These standard anti-diabetic medications are far from fulfilling the immense needs of patients suffering from high blood sugar levels. Insulin, for example, has to be administered by injection or via a continuous intravenous pump. Small-molecule antidiabetic drugs, such as sulphonylurea and metformin, can be administered orally, but they are associated with side effects, such as gastrointestinal irritation and increased burden to the liver. Inconvenience of administration routes and undesirable side effects over extended duration of treatment greatly compromise patients' quality of life and render adherence to the therapeutic regimens rather challenging. As a result, alternative or supplementary means for lowering blood sugar are constantly sought after to satisfy the unmet patient needs.

Herbal medicine and nutritional supplements have long been widely applied by many cultures throughout the world to improve or maintain bodily functions. Traditional Chinese Medicine relies heavily on empirically-tested folk herbal medicines to treat human illnesses. Several herbs from Traditional Chinese Medicine possess hypoglycemic (or blood sugar lowering) effects, including *Cyclocarya paliurus* (wheel wingnut) leaves, *Mori Cortex* (mulberry bark), *Dendrobii Caulis*, and *Citri Reticulatae Pericarpium* (dried tangerine peel).

All references described herein are incorporated by reference in their entirety.

BRIEF SUMMARY

The present invention provides a health care composition (or a health-enhancing composition, such as a pharmaceutical composition or a nutritional composition) comprising (including consisting essentially of or consisting of) *Cyclocarya paliurus* leaves and one or more herbs selected from the group consisting of *Mori Cortex, Dendrobii Caulis* and *Citri Reticulatae Pericarpium*. The invention also provides health care compositions (e.g., a pharmaceutical composition or a nutritional composition) comprising two or more herbs selected from the group consisting of *Mori Cortex, Dendrobii Caulis, Citri Reticulatae Pericarpium, Puerariae lobatae Radix* and *Polygonati odorati Rhizoma*, optionally the composition may further comprise one or more herbs selected from the group consisting of *Cyclocarya paliurus* leaves, *Dioscoreae Rhizoma, Poria, Lycii Fructus, Angelicae sinensis Radix, Ginseng Radix et Rhizoma* and *Rhodiolae Crenulatae Radix et Rhizoma*.

In some aspects, provided is an herbal extract composition comprising (including consisting essentially of or consisting of) an extract of *Cyclocarya paliurus* leaves and one or more herbs selected from the group consisting of *Mori Cortex, Dendrobii Caulis* and *Citri Reticulatae Pericarpium*, a gel capsule comprising the herbal extract composition, methods for preparing the herbal extract composition and the gel capsule thereof, and uses of the herbal extract composition and the gel capsule to reduce blood sugar and to treat or prevent a disease or condition responsive to lowering blood sugar, such as diabetes.

In some embodiments, provided is an herbal extract composition comprising (including consisting essentially of or consisting of) an extract of *Cyclocarya paliurus* leaves, *Mori Cortex, Dendrobii Caulis* and *Citri Reticulatae Pericarpium*. In some embodiments, provided is an herbal extract composition comprising an extract of *Cyclocarya paliurus* leaves, *Mori Cortex* (mulberry bark), *Dendrobii Caulis* and *Citri Reticulatae Pericarpium* (dried tangerine peel) at a relative proportion (by weight) of about 1-97%:1-97%:1-97%:1-97%, about 10-70%:10-70%:10-70%:10-70%, about 20-60%:20-60%:10-50%:10-50%, about 30-40%:30-40%:10-30%:10-30%, or about 35%:35%:20%:10%.

In some embodiments, provided is an herbal extract composition comprising (including consisting essentially of or consisting of) an extract of *Cyclocarya paliurus* leaves and one, two or three herbs selected from the group consisting of *Mori Cortex, Dendrobii Caulis* and *Citri Reticulatae Pericarpium*. In some embodiments, the herbal extract composition comprises (including consists essentially of or consists of) an extract of *Cyclocarya paliurus* leaves and two herbs selected from the group consisting of *Mori Cortex, Dendrobii Caulis* and *Citri Reticulatae Pericarpium*. In some embodiments, the herbal extract composition comprises (including consists essentially of or consists of) an extract of *Cyclocarya paliurus* leaves and one herb selected from the group consisting of *Mori Cortex, Dendrobii Caulis* and *Citri Reticulatae Pericarpium*. In one embodiment, the herbal extract composition comprises (including consists essentially of or consists of) an extract of *Cyclocarya paliurus* leaves, *Mori Cortex* and *Dendrobii Caulis*. In one embodiment, the herbal extract composition comprises (including consists essentially of or consists of) an extract of *Cyclocarya paliurus* leaves and *Dendrobii Caulis*. In one embodiment, the herbal extract composition comprises (including consists essentially of or consists of) an extract of *Cyclocarya paliurus* leaves and *Citri Reticulatae Pericarpium*.

In some embodiments of any of the herbal extract compositions, the herbal extract composition further comprises an extract of one or more herbs selected from the group consisting of *Polygonati Rhizoma, Laminariae Thallus/Eckloniae Thallus, Mume Fructus, Notoginseng Radix et Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix*, Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

The herbal extract compositions may be prepared, for example, by a method comprising extracting a mixture of *Cyclocarya paliurus* leaves and one, two or three herbs selected from the group consisting of *Mori Cortex, Dendrobii Caulis* and *Citri Reticulatae Pericarpium* with boiling water to obtain an aqueous extract; concentrating the aqueous extract to obtain a concentrated mixture; obtaining a liquid portion of the concentrated mixture; and drying said extract to produce an herbal extract composition.

Also provided is a method of preparing an oral formulation comprising mixing an herbal extract composition detailed herein with one or more pharmaceutically acceptable carrier or excipients. In some embodiments, the pharmaceutically acceptable excipients independently selected from the group consisting of pregelatinized starch, β-cyclodextrin, maltodextrin, Carbopol, microcrystalline cellulose, hydroxypropylmethylcellulose, low-substituted hydroxypropylcellulose, polyethylene glycol (PEG), sodium carboxymethyl cellulose, methylcellulose, ethylcellulose, mannitol, cross-linked sodium carboxymethyl cellulose, lactose, polyvinylpyrrolidone (PVP), magnesium stearate, talc, silica powder, aspartame, sodium bicarbonate, and sodium carbonate.

Also provided herein are methods of making the herbal extract composition described herein. In some embodiments, provided is a method for preparing an herbal extract composition comprising an extract of *Cyclocarya paliurus* leaves and one, two or three herbs selected from the group consisting of *Mori Cortex* (mulberry bark), *Dendrobii Caulis* and *Citri Reticulatae Pericarpium* (dried tangerine peel), the method comprising: (a) extracting a mixture of *Cyclocarya paliurus* leaves, *Mori Cortex, Dendrobii Caulis* and *Citri Reticulatae Pericarpium* with water (e.g., boiling water) to obtain an aqueous extract; (b) concentrating the aqueous extract to obtain a concentrated mixture; (c) obtaining a liquid portion of said concentrated mixture; and (d) optionally drying (e.g., spray-drying) said extract to produce an herbal composition. In some embodiments, the method for preparing an herbal extract composition comprising an extract of *Cyclocarya paliurus* leaves and one, two or three herbs selected from the group consisting of *Mori Cortex* (mulberry bark), *Dendrobii Caulis* and *Citri Reticulatae Pericarpium* (dried tangerine peel), comprises: (a) providing a mixture of *Cyclocarya paliurus* leaves, *Mori Cortex, Dendrobii Caulis* and *Citri Reticulatae Pericarpium*; (b) extracting said mixture with water to obtain an aqueous extract; (c) concentrating the aqueous extract to obtain a concentrated mixture; (d) obtaining a liquid portion of said concentrated mixture; and (e) drying said extract to produce an herbal extract composition. In some embodiments, the mixture comprises *Cyclocarya paliurus* leaves, *Mori Cortex, Dendrobii Caulis* and *Citri Reticulatae Pericarpium* in a relative proportion (by weight) of about 30-40% (w) *Cyclocarya paliurus* leaves, about 30-40% (w) *Mori Cortex*, about 10-30% (w) *Dendrobii Caulis* and about 10-30% (w) *Citri Reticulatae Pericarpium*.

In some embodiments according to any one of the methods described above, the extracting step comprises extracting the mixture with a first portion of water (e.g., boiling water) for about 1-3 hours (such as 2 hours) to obtain a first aqueous extract; further extracting said mixture with a second portion of water (e.g., boiling water) for about 0.5-1.5 hours (such as 1 hour) to obtain a second aqueous extract; and combining said first aqueous extract and said second aqueous extract to give the aqueous extract. In some embodiments, the first portion of boiling water is about 8-15 (such as about 12) times (by weight) of said mixture of *Cyclocarya paliurus* leaves and one, two or three herbs selected from the group consisting of *Mori Cortex, Dendrobii Caulis* and *Citri Reticulatae Pericarpium*, and the second portion of boiling water is about 8-12 (such as about 10) times (by weight) of said mixture of *Cyclocarya paliurus* leaves and one, two or three herbs selected from the group consisting of *Mori Cortex, Dendrobii Caulis* and *Citri Reticulatae Pericarpium*. In some embodiments, the method further comprises filtering the aqueous extract though a filter (such as a 40-200-mesh filter, e.g., a 200-mesh filter).

In some embodiments according to any one of the methods described above, the method further comprises a step of removing heavy metal from the herbal mixture. In some embodiments, the step of removing herbal metal can comprise washing the raw materials of *Cyclocarya paliurus* leaves and one, two or three herbs selected from the group consisting of *Mori Cortex, Dendrobii Caulis* and *Citri Reticulatae Pericarpium* prior to mixing them together. In some embodiments, the step of removing herbal metal can take place during or after the extraction step. For example, in some embodiments, the extracting step comprises extracting the mixture with a first portion of boiling water for about 1-3 (such as about 2) hours to obtain a first aqueous extract, and the first aqueous extract is subject to heavy metal removal. In some embodiments, the extracting step comprises extracting the mixture with a first portion of boiling water for about 1-3 (such as about 2) hours to obtain a first aqueous extract; further extracting said mixture with a second portion of boiling water for about 0.5-2 (such as about 1) hours to obtain a second aqueous extract, and each of the first and second aqueous extract are subject to heavy metal removal separately. In some embodiments, the extracting step comprises extracting the mixture with a first portion of boiling water for 1-3 (such as about 2) hours to obtain a first aqueous extract; further extracting said mixture with a second portion of boiling water for 0.5-2 (such as about 1) hours to obtain a second aqueous extract; and combining said first aqueous extract and said second aqueous extract to give the aqueous extract, and the combined extract is subject to heavy metal removal. The heavy metal removal steps comprises, for example, adding potassium carbonate to the aqueous extract and filtering the (first, second, and/or combined) aqueous extract through a filter (such as 200-40 mesh filter).

In some embodiments according to any one of the methods described above, the concentrating step comprises heating the aqueous extract (for example at about 50~90° C. or 65~80° C.) under a vacuum (for example under a vacuum of about −0.08~−0.02 MPa or −0.06~−0.04 MPa) to obtain a concentrated mixture (for example a concentrated mixture having a relative density of about 1.0-1.2 (e.g., about 1.05, measured at about 60° C.)).

In some embodiments according to any one of the methods described above, the liquid portion of the concentrated mixture is obtained after allowing the concentrated mixture to stand at a refrigerated condition (for example at about 0-6° C., or about 4° C.) for at least 6 hours (such as at least about 10 hours).

In some embodiments according to any one of the methods described above, the liquid portion of the concentrated mixture is subject to further heavy metal removal steps comprising optionally adding chitosan to the mixture, allowing the liquid portion to stand for at least 6 hours (such as at least about 12 hours), and centrifuging the liquid portion (e.g. at about 4000-8000 rpm for about 15 minutes).

In some embodiments according to any one of the methods described above, the step of mixing said liquid portion with a pharmaceutically acceptable carrier or excipient (e.g., β-cyclodextrin, maltodextrin, or lactose) comprises heating said liquid, portion with an amount of the pharmaceutically acceptable carrier or excipient to about 60-100° C. (e.g., about 80° C.) and stir-mixing to obtain an extract.

In some embodiments according to any one of the methods described above, the step of drying comprises spray-drying the pharmaceutically acceptable carrier or excipient-containing extract in a spray-drying chamber having an in-flow temperature at about 190° C.±10° C. and an out-flow temperature of about 90° C.±10° C. and producing an herbal extract composition.

In some embodiments according to any one of the methods described above, the method further comprises packing and sealing the herbal extract composition in a sterile package.

Also provided herein are herbal extract compositions prepared by a method according to any one of the methods described above.

The herbal extract compositions described above can be used further to make a capsule, such as a gel capsule. For example, in some embodiments, provided is a method for preparing a gel capsule comprising an herbal extract, a microcrystalline cellulose and calcium hydrogen phosphate, said method comprising: (a) mixing an herbal extract composition comprising (including consisting essentially of or consisting of) an extract of *Cyclocarya paliurus* and one, two or three herbs selected from the group consisting of *Mori Cortex, Dendrobii Caulis* and *Citri Reticulatae Pericarpiu* with a microcrystalline cellulose and calcium hydrogen phosphate to obtain a first mixture; (b) treating a portion of said first mixture with an alcoholic solvent (for example 95% ethanol) to obtain a wet granule; drying the wet granule to obtain a dry granule; (c) mixing said dry granule with magnesium stearate or silica to obtain a second mixture; and (d) filling a portion of said second mixture in a gel capsule. In some embodiments of the method for preparing a gel capsule comprising an herbal extract, a microcrystalline cellulose and calcium hydrogen phosphate, the method comprises: (a) providing an herbal extract composition comprising (including consisting essentially of or consisting of) an extract of *Cyclocarya paliurus* and one, two or three herbs selected from the group consisting of *Mori Cortex, Dendrobii Caulis* and *Citri Reticulatae Pericarpiu*; (b) mixing said herbal extract composition with a microcrystalline cellulose and calcium hydrogen phosphate to obtain a first mixture; (c) treating a portion of said first mixture with an alcoholic solvent (for example 95% ethanol) to obtain a wet granule; (d) drying the wet granule to obtain a dry granule; (e) mixing said dry granule with magnesium stearate or silica to obtain a second mixture; and (f) filling a portion of said second mixture in a gel capsule.

In some embodiments, the herbal extract is made by any one of the methods described above. Thus, for example, in some embodiments, provided is a method for preparing a gel capsule comprising an herbal extract, a microcrystalline cellulose and calcium hydrogen phosphate, said method comprising: (a) mixing an herbal extract composition with a microcrystalline cellulose and calcium hydrogen phosphate to obtain a first mixture; (b) treating a portion of said first mixture with an alcoholic solvent (for example 95% ethanol) to obtain a wet granule; drying the wet granule to obtain a dry granule; (c) mixing said dry granule with magnesium stearate or silica to obtain a second mixture; and (d) filling a portion of said second mixture in a gel capsule, wherein the herbal extract composition is produce by a method comprising: (i) extracting a mixture of *Cyclocarya paliurus* leaves and one, two or three herbs selected from the group consisting of *Mori Cortex, Dendrobii Caulis* and *Citri Reticulatae Pericarpium* with boiling water to obtain an aqueous extract; (ii) concentrating the aqueous extract to obtain a concentrated mixture; (iii) obtaining a liquid portion of said concentrated mixture; (iv) optionally mixing said liquid portion with β-cyclodextrin, maltodextrin, or lactose to obtain an extract; (v) optionally spray-drying said extract to produce an herbal extract composition. In some embodiments, provided is a method for preparing a gel capsule comprising an herbal extract, a microcrystalline cellulose and calcium hydrogen phosphate, said method comprising: (a) extracting a mixture of *Cyclocarya paliurus* leaves and one, two or three herbs selected from the group consisting of *Mori Cortex, Dendrobii Caulis* and *Citri Reticulatae Pericarpium* with boiling water to obtain an aqueous extract; (b) concentrating the aqueous extract to obtain a concentrated mixture; (c) obtaining a liquid portion of said concentrated mixture; (d) optionally mixing said liquid portion with β-cyclodextrin, maltodextrin, or lactose to obtain an extract; (f) optionally drying (e.g., spray-drying) said extract to produce an herbal extract composition; (g) mixing said herbal extract composition with a microcrystalline cellulose and calcium hydrogen phosphate to obtain a first mixture; (h) treating a portion of said first mixture with an alcoholic solvent (for example 95% ethanol) to obtain a wet granule; drying the wet granule to obtain a dry granule; (i) mixing said dry granule with magnesium stearate or silica to obtain a second mixture; and (j) filling a portion of said second mixture in a gel capsule.

In some embodiments according to any one of the methods of preparing a gel capsule described above, the method comprises weighing a predetermined amount of the herbal extract composition, a predetermined amount of microcrystalline cellulose and a predetermined amount of calcium hydrogen phosphate prior to mixing the components together. In some embodiments, the various components are mixed for about 1-10 minutes to obtain a first mixture, wherein said first mixture is a uniform mixture.

In some embodiments according to any one of the methods of preparing a gel capsule described above, the wet granule are sieved (for example through a 20-10-mesh sieve) prior to the drying step.

In some embodiments according to any one of the methods of preparing a gel capsule described above, the drying of the wet granule comprises drying the wet granule at an elevated temperature (for example at about 50° C.-80° C. or about 70° C.±5° C.) to obtain a dry granule (for example a dry granule contains less than about 5% water). In some embodiments, the dry granules are further sieved (for example through a 30-10-mesh sieve or a 20-mesh sieve).

In some embodiments according to any one of the methods of preparing a gel capsule described above, the dry granule and the magnesium stearate are further mixed for about 10-30 minutes to obtain a second mixture, wherein said second mixture is a uniform mixture.

In some embodiments according to any one of the methods of preparing a gel capsule described above, the filling step comprises filing a portion of about 0.3 g of said second mixture in a gel capsule, wherein said gel capsule is a size 1 gel capsule. In some embodiments, the method further comprises polishing the gel capsule, packaging and/or testing for quality control.

Also provided is a gel capsule comprising an extract of *Cyclocarya paliurus* leaves, wherein the gel capsule is prepared by any one of the methods described above.

Further provided is a health care composition (such as nutritional compositions or pharmaceutical compositions) comprising any one of the herbal extract compositions or gel capsules described above. In some embodiments, the nutritional composition or pharmaceutical composition further comprises a nutraceutically or pharmaceutically acceptable carrier. The compositions are useful, for example, for lowering blood sugar, promoting general health, and improving quality of life. The compositions are also useful for treating hyperglycemia, hypertension and/or hyperlipidemia in a subject in need thereof.

In one aspect, provided is a method of lowering blood sugar in an individual (such as a human individual), comprising administering to the individual an effective amount of a health care composition (such as a pharmaceutical composition or a nutritional composition) or any one of the herbal extract composition or gel capsules described above.

In one aspect, provided is a method of providing nutritional supplement to an individual (such as a human individual), comprising administering to the individual an effective amount of a nutritional composition or any one of the herbal extract composition or gel capsules described above.

In one aspect, provided is a method of treating a disease or condition responsive to lowering of blood sugar in an individual (such as a human individual), comprising administering to the individual an effective amount of a pharmaceutical composition or any one of the herbal extract composition or gel capsules described above. In some embodiments, the disease is diabetes.

In one aspect, provided is a method of t treating hyperglycemia, hypertension and/or hyperlipidemia in an individual (such as a human individual), comprising administering to the individual an effective amount of a pharmaceutical composition or any one of the herbal extract composition or gel capsules described above.

Also provided is a use of any one of the herbal extracts described above for the manufacture of medicament for lowering blood sugar, treating a disease or condition (e.g., diabetes, hyperglycemia, hypertension or hyperlipidemia), or providing nutritional supplement.

Further provided is any one of the compositions described herein for use in lowering blood sugar, treating a disease or condition (e.g., diabetes, hyperglycemia, hypertension or hyperlipidemia), or providing nutritional supplement, to an individual in need thereof.

BRIEF DESCRIPTION OF THE DRAWINGS

FIG. 11 shows the names in Chinese characters for some of the Chinese herbal medicines described herein.

DETAILED DESCRIPTIONS

Figure 1:
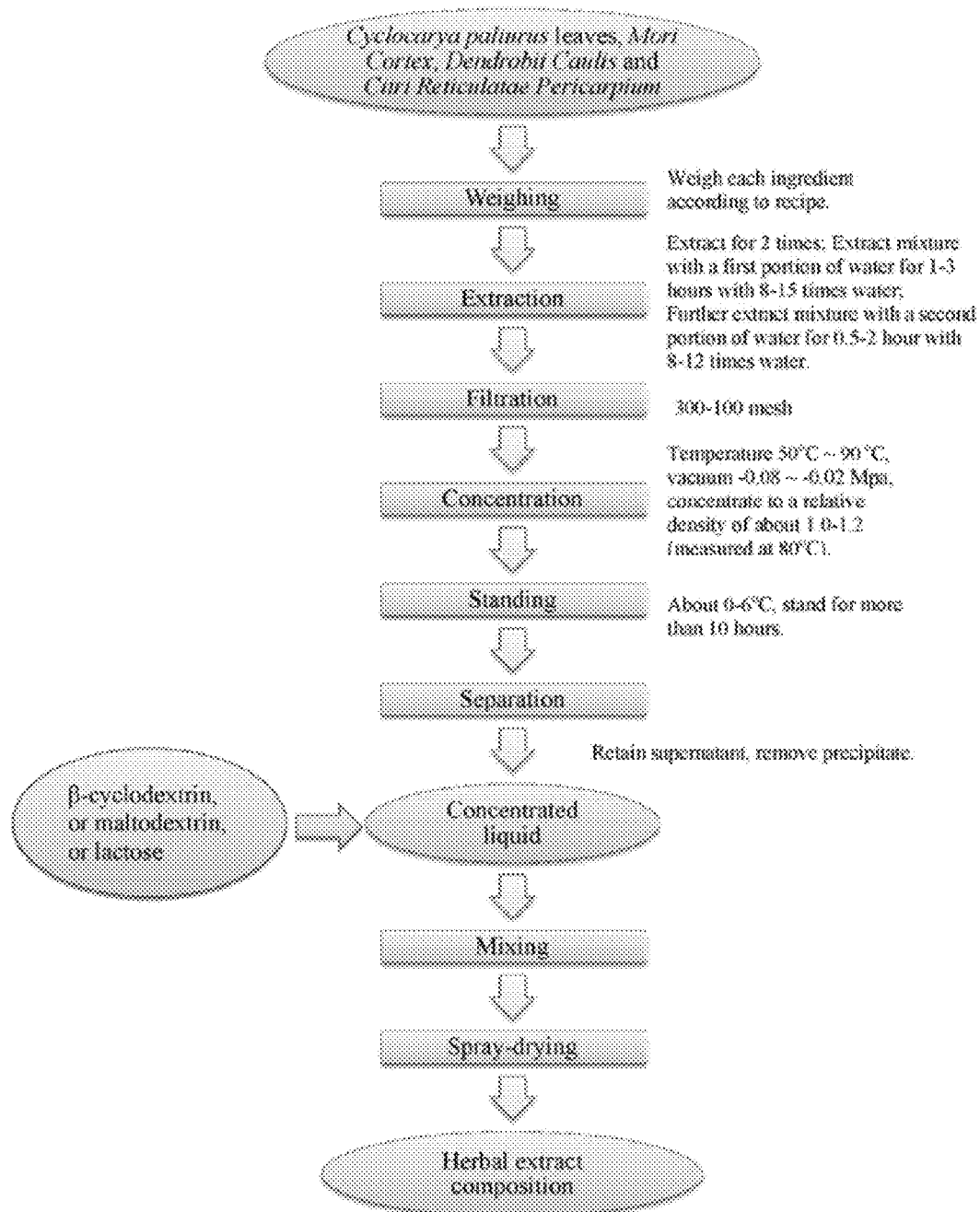
FIG. 1 and FIG. 2 show schematic flow charts of exemplary embodiments of a method for preparing an herbal extract composition comprising (including consisting essentially of or consisting of) an extract of *Cyclocarya paliurus* leaves, *Mori Cortex*, *Dendrobii Caulis* and *Citri Reticulatae Pericarpium*.

The present invention provides a health care composition (or a health-enhancing composition, e.g., a pharmaceutical composition or a nutritional composition) comprising (including consisting essentially of or consisting of) *Cyclocarya paliurus* leaves and one or more herbs selected from the group consisting of *Mori Cortex, Dendrobii Caulis* and *Citri Reticulatae Pericarpium*. Also provided are methods of using any of the compositions in lowering blood sugar, treating a disease or condition (e.g., diabetes, hyperglycemia, hypertension or hyperlipidemia), or providing nutritional supplement, to an individual in need thereof. Further provided are methods and processes for preparing or manufacturing the compositions described herein.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

Unless otherwise noted, technical terms are used according to conventional usage.

The compositions and methods of the present invention may comprise, consist of, or consist essentially of the essential elements and limitations of the invention described herein, as well as any additional or optional ingredients, components, or limitations described herein or otherwise useful.

It is understood that aspects and embodiments of the invention described herein include "comprising," "consisting of," and "consisting essentially of" aspects and embodiments. For example, for all compositions described herein, and all methods using or making a composition described herein, the compositions can either comprise the listed components or steps, or can "consist essentially of" the listed components or steps. A composition consisting essentially of a list of components contains at least 60% (e.g., by weight) of the listed components. In some embodiments, a composition consisting essentially of a list of components contains at least 65%, 70%, 75%, 80%, 85%, 90% or 95% (e.g., by weight) of the listed components. In some embodiments, a composition consisting essentially of a list of components contains at least 95%, 96%, 97%, 98% or 99% (e.g., by weight) of the listed components. In some embodiments, a composition consisting essentially of a list of components contains about 99%, about 99.5% or about 99.9% (e.g., by weight) of the listed components. For example, in a pharmaceutical composition consisting essentially of a list of herbal components (e.g., *Cyclocarya paliurus* leaves, *Mori Cortex*, *Dendrobii Caulis* and *Citri Reticulatae Pericarpium*), the listed herbal components account for at least 60% (e.g., by weight) of all of the active ingredients. In some embodiments, the pharmaceutical composition contains at least 70%, 85%, 90%, 95%, or 99% (by weight) of list of herbal components (e.g., *Cyclocarya paliurus* leaves, *Mori Cortex*, *Dendrobii Caulis* and *Citri Reticulatae Pericarpium*). In some embodiments, the pharmaceutical composition contains about 99%, about 99.5% or about 99.9% (by weight) of list of herbal components (e.g., *Cyclocarya paliurus* leaves, *Mori Cortex*, *Dendrobii Caulis* and *Citri Reticulatae Pericarpium*).

As used herein, a composition comprising an herb (e.g., *Cyclocarya paliurus* leaves) means the composition includes (inclusive or open-ended) the herb in its raw form or processed form, for example, crushed and sieved parts or particles, or extracts of the herb.

When a percentage (or relative amount) of an herb is stated for a composition obtained by processing a mixture of more than one herbs, the percentage or relative amount indicates the proportion of the herb in the mixture before the mixture is processed. For example, when an herbal extract composition obtained by extracting a mixture of *Cyclocarya paliurus* leaves and other herbs is stated to comprise about 50% (by weight) of *Cyclocarya paliurus* leaves, the mixture comprises about 50% (by weight) of *Cyclocarya paliurus* leaves before extraction.

Health Care Compositions

*Cyclocarya paliurus* is also known as wheel wingnut, sweet tea tree, or in Traditional Chinese Medicine Qing qian liu. A native deciduous plant of China and the sole species in the genus of flowering plants named *Cyclocarya* in the family Juglandaceae, *Cyclocarya paliurus* is found in the foggy high-mountain regions in southern China, especially in the Jiang Xi Province. The leaves of *Cyclocarya paliurus* are particularly suitable for use in nutritional and pharmaceutical compositions for human consumption, because the leaves have a sweet flavor and contain many chemical constituents with health benefits, including proteins, polysaccharides, triterpenoids, flavonoids, and phenolic compounds. In the present invention, the term "*Cyclocarya paliurus*" refers to the plant or any part of the plant, including but not limited to its leaves, bark, stem, root, buds and flowers. Additionally, the plant parts of *Cyclocarya paliurus* can be young or old, fresh or dried, raw or processed. Indications and properties of *Cyclocarya paliurus* leaves as a traditional Chinese medicine include but are not limited to the following: slightly bitter, pungent, neutral; acts to tonify spleen and resolve dampness, clear heat and soothe viscera, relieve Qi stagnancy in liver, and nourish kidney Yin; and is effective in relieving obesity due to non-invigorating spleen, phlegm turbidity, preference in fatty, sweet, and heavy-taste food, laziness to move, food retention, liver depression and Qi stagnation.

*Mori Cortex* is also known as *Cortex Mori, Cortex Mori Radicis, Morus* bark, mulberry bark, or in Traditional Chinese Medicine Sang bai pi. The herb is prepared from the root epidermis of the plant *Morus alba*, or white mulberry, which is a short-lived, fast growing plant in the family of Moraceae. A native plant of China, *Morus alba* is now widely cultivated in many parts of the world to feed silkworms in the commercial production of silk. *Mori Cortex* is slightly sweet in flavor. Small molecules extracted from *Mori Cortex* have a wide range of health benefits, including antibiotic, antioxidant, hypoglycemic and antidepressant effects. In the present invention, the term "*Mori Cortex*" refers to the root bark of *Morus alba*, in raw or processed conditions, and in an exemplary embodiment, the root bark is dried. Indications and properties of *Mori Cortex* as a traditional Chinese medicine include but are not limited to the following: purging lungs to relieve dyspnea, inducing diuresis to alleviate edema; indicated for treating cough and dyspnea due to lung heat, face edema, and dysuria; effective in decreasing blood pressure, relieving dyspnca, calming and easing pain, anti-inflammation, anti-bacteria, and lowing blood sugar.

*Dendrobii Caulis* is also known as *Caulis Dendrobii* and in Traditional Chinese Medicine Shi hu. The herb is prepared from the stem of certain orchid (*Dendrobium*) species, including but not limited to *Dendrobium nobile* Lindl., *Dendrobium loddigesii* Rolfe, *Dendrobium candidum* Wall. Ex Lindl., *Dendrobium chrysanthum* Wall. Ex Lindl., and *Dedrobium fimbriatum* Hook. Var. *oculatum* Hook. In particular, *Dendrobium nobile* Lindl. is considered as one of the 50 fundamental herbs in Traditional Chinese Medicine. In the present invention, the term "*Dendrobii* Cauli" refers to the stem of common *Dendrobium* species used in Traditional Chinese Medicine as described above, and such stem is in raw or processed, fresh or dried conditions. Indications and properties of *Dendrobii Caulis* as a traditional Chinese medicine include but are not limited to the following: sweet, slightly salty, bland, cold; entering stomach, kidney and lung meridians; acts to nourish stomach and promote saliva secretion, nourish Yin and clear heat; indicated for treating Yin deficiency and depleted fluids, thirst, dryness in mouth and throat, bad appetite and dysemesia, deficiency-heat after disease, and dull vision.

*Citri Reticulatae Pericarpium* is also known as *Pericarpium Citri* Reticulate, dried tangerine peel, aged tangerine peel, ripe tangerine rind, or in Traditional Chinese Medicine, Chen pi. *Citri Reticulatae Pericarpium* is usually prepared by drying tangerine (or mandarin) peel, and aging the peel by storing it dry. With a pungent and bitter taste, *Citri Reticulatae Pericarpium* is a common ingredient in traditional Chinese medicine and Chinese cuisine. Tangerine and other citrus peels normally contain essential oils with health benefits. In the present invention, the term "*Citri Reticulatae Pericarpium*" refers to dried tangerine peel in raw or processed conditions, and in an exemplary embodiment, the tangerine peel is aged. Indications and properties of *Citri Reticulatae Pericarpium* as a traditional Chinese medicine include but are not limited to the following: bitter, pungent, warm; entering lung and spleen meridians; having functions of regulating Qi and strengthening spleen functions, drying dampness and resolving phlegm; indicated for treating Qi stagnation or food retention, bad appetite, vomiting and diarrhea, coughing and copious sputum.

The invention provides a health care composition (or a health-enhancing composition, e.g., a pharmaceutical composition or a nutritional composition) comprising (including consisting essentially of or consisting of) *Cyclocarya paliu-* rus leaves and one or more herbs selected from the group consisting of *Mori Cortex, Dendrobii Caulis* and *Citri Reticulatae Pericarpium*. In some instances, the composition comprises (including consists essentially of or consists of) parts or particles obtained by mechanically processing the herbs. For example, the composition may comprise crushed parts of the herbs mixed together in packet (e.g., a tea bag). In some instances, the composition comprises (including consists essentially of or consists of) substances extracted from *Cyclocarya paliurus* leaves and the other herbs, for example, by using a method described herein for preparing an herbal extract composition. The health care composition disclosed herein comprising the herbs may provide synergistic effect in lowering blood sugar, while avoiding excessive toxicity often associated with long-term usage of Traditional Chinese Medicine due to factors such as heavy metal contamination and impurities.

In some embodiments, the health care composition comprises (including consists essentially of or consists of) *Cyclocarya paliurus* leaves and one, two or three herbs selected from the group consisting of *Mori Cortex, Dendrobii Caulis* and *Citri Reticulatae Pericarpium*. In some embodiments, the health care composition comprises (including consists essentially of or consists of) *Cyclocarya paliurus* leaves and two herbs selected from the group consisting of *Mori Cortex, Dendrobii Caulis* and *Citri Reticulatae Pericarpium*. In some embodiments, the health care composition comprises (including consists essentially of or consists of) *Cyclocarya paliurus* leaves and one herb selected from the group consisting of *Mori Cortex, Dendrobii Caulis* and *Citri Reticulatae Pericarpium*.

In some preferred embodiments, the health care composition (e.g., a pharmaceutical composition or a nutritional composition) comprises (including consists essentially of or consists of) *Cyclocarya paliurus* leaves, *Mori Cortex, Dendrobii Caulis* and *Citri Reticulatae Pericarpium*. In some embodiments, the health care composition consists essentially of *Cyclocarya paliurus* leaves, *Mori Cortex, Dendrobii Caulis* and *Citri Reticulatae Pericarpium*. In some embodiments, the health care composition consists essentially of *Cyclocarya paliurus* leaves, *Mori Cortex, Dendrobii Caulis* and *Citri Reticulatae Pericarpium*, wherein the *Cyclocarya paliurus* leaves, *Mori Cortex, Dendrobii Caulis* and *Citri Reticulatae Pericarpium* have a relative proportion (by weight) of about 30-40% (w) *Cyclocarya paliurus* leaves, about 30-40% (w) *Mori Cortex*, about 10-30% (w) *Dendrobii Caulis* and about 10-30% (w) *Citri Reticulatae Pericarpium*. In some embodiments, the composition consists of *Cyclocarya paliurus* leaves, *Mori Cortex, Dendrobii Caulis* and *Citri Reticulatae Pericarpium*, wherein the *Cyclocarya paliurus* leaves, *Mori Cortex, Dendrobii Caulis* and *Citri Reticulatae Pericarpium* have a relative proportion (by weight) of about 30-40% (w) *Cyclocarya paliurus* leaves, about 30-40% (w) *Mori Cortex*, about 10-30% (w) *Dendrobii Caulis* and about 10-30% (w) *Citri Reticulatae Pericarpium*. In some embodiments, the composition comprises about 1-97% (w) *Cyclocarya paliurus* leaves, about 1-97% (w) *Mori Cortex*, about 1-97% (w) *Dendrobii Caulis* and about 1-97% (w) *Citri Reticulatae Pericarpium*. In some embodiments, the composition comprises about 10-70% (w) *Cyclocarya paliurus* leaves, about 10-70% (w) *Mori Cortex*, about 10-70% (w) *Dendrobii Caulis* and about 10-70% (w) *Citri Reticulatae Pericarpium*. In some embodiments, the composition comprises about 20-60% (w) *Cyclocarya paliurus* leaves, about 20-60% (w) *Mori Cortex*, about 10-50% (w) *Dendrobii Caulis* and about 10-50% (w) *Citri Reticulatae Pericarpium*. In some embodiments, the composition comprises about 30-40% (w) *Cyclocarya paliurus* leaves, about 30-40% (w) *Mori Cortex*, about 10-30% (w) *Dendrobii Caulis* and about 10-30% (w) *Citri Reticulatae Pericarpium*. In some embodiments, the composition comprises about 35% (w) *Cyclocarya paliurus* leaves, about 35% (w) *Mori Cortex*, about 20% (w) *Dendrobii Caulis* and about 10% (w) *Citri Reticulatae Pericarpium*. In some embodiments of any of the compositions, the composition further comprises one or more herbs selected from the group consisting of *Polygonati Rhizoma, Laminariae Thallus/Eckloniae Thallus, Mume Fructus, Notoginseng Radix et Rhizoma, Ligustri lucidi Fructus, Corni Fructus, Rhizoma, Atractylodis Rhizoma, Scrophulariae Radix, Rehmanniae Radix, Paeoniae Radix alba, Panacis Quinquefolii Radix, Aloe, Schisandrae chinensis Fructus, Ophiopogonis Radix*, Prepared Rhubarb, *Anemarrhenae Rhizoma, Tribull Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In some embodiments, the health care composition (e.g., a pharmaceutical composition or a nutritional composition) comprises (including consists essentially of or consists of) *Cyclocarya paliurus* leaves and *Dendrobii Caulis*. In some embodiments, the composition comprises about 1-99% (w) *Cyclocarya paliurus* leaves and about 1-99% (w) *Dendrobii Caulis*. In some embodiments, the composition comprises about 20-80% (w) *Cyclocarya paliurus* leaves and about 20-80% (w) *Dendrobii Caulis*. In some embodiments, the composition comprises about 30-70% (w) *Cyclocarya paliurus* leaves and about 30-70% (w) *Dendrobii Caulis*. In some embodiments, the composition comprises about 40-60% (w) *Cyclocarya paliurus* leaves and about 40-60% (w) *Dendrobii Caulis*. In some embodiments, the health care composition consists essentially of *Cyclocarya paliurus* leaves and *Dendrobii Caulis*. In some embodiments, the composition further comprises one or more herbs selected from the group consisting of *Polygonati odorati Rhizoma, Dioscoreae Rhizoma, Puerariae lobatae Radix, Poria*, and *Mori Cortex*. In some embodiments, the composition comprises about 1-98% (w) *Cyclocarya paliurus* leaves, about 1-98% (w) *Dendrobii Caulis* and about 1-98% (w) of one or more herbs selected from the group consisting of *Polygonati odorati Rhizoma, Dioscoreae Rhizoma, Puerariae lobatae Radix, Poria*, and *Mori Cortex*. In some embodiments, the composition comprises about 10-80% (w) *Cyclocarya paliurus* leaves, about 10-80% (w) *Dendrobii Caulis* and about 10-80% (w) of one or more herbs selected from the group consisting of *Polygonati odorati Rhizoma, Dioscoreae Rhizoma, Puerariae lobatae Radix, Poria*, and *Mori Cortex*. In some embodiments, the composition comprises about 20-60% (w) *Cyclocarya paliurus* leaves, about 20-60% (w) *Dendrobii Caulis* and about 20-60% (w) of one or more herbs selected from the group consisting of *Polygonati odorati Rhizoma, Dioscoreae Rhizoma, Puerariae lobatae Radix, Poria*, and *Mori Cortex*. In some embodiments, the composition further comprises one or more herbs selected from the group consisting of *Lycii Fructus, Ginseng Radix et Rhizoma, Citri Reticulatae Pericarpium, Angelicae sinensis Radix*, and *Rhodiolae Crenulatae Radix et Rhizoma*. In some embodiments, the composition further comprises one or more herbs selected from the group consisting of *Polygonati odorati Rhizoma, Dioscoreae Rhizoma, Puerariae lobatae Radix, Poria*, and *Mori Cortex*, and one or more herbs selected from the group consisting of *Lycii Fructus, Ginseng Radix et Rhizoma, Citri Reticulatae Pericarpium, Angelicae sinensis Radix*, and *Rhodiolae Crenulatae Radix et Rhizoma*.

In some of these embodiments, the composition comprises about 10-40% (w), about 20-30% (w), or about 25% (w) of one or more herbs selected from the group consisting of *Lycii Fructus, Ginseng Radix et Rhizoma, Citri Reticulatae Pericarpium, Angelicae sinensis Radix*, and *Rhodiolae Crenulatae Radix et Rhizoma*. In some embodiments of any of the compositions, the composition further comprises one or more herbs selected from the group consisting of *Polygonati Rhizoma, Laminariae Thallus/Eckloniae Thallus, Mume Fructus, Notoginseng Radix et Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix*, Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition (e.g., a pharmaceutical composition or a nutritional composition) comprises (including consists essentially of or consists of) *Cyclocarya paliurus* leaves and *Citri Reticulatae Pericarpium*. In some embodiments, the composition comprises about 1-99% (w) *Cyclocarya paliurus* leaves and about 1-99% (w) *Citri Reticulatae Pericarpium*. In some embodiments, the composition comprises about 10-80% (w) *Cyclocarya paliurus* leaves and about 10-90% (w) *Citri Reticulatae Pericarpium*. In some embodiments, the composition comprises about 20-70% (w) *Cyclocarya paliurus* leaves and about 20-70% (w) *Citri Reticulatae Pericarpium*. In some embodiments, the composition comprises about 30-40% (w) *Cyclocarya paliurus* leaves and about 10-20% (w) *Citri Reticulatae Pericarpium*. In some embodiments, the health care composition consists essentially of *Cyclocarya paliurus* leaves and *Citri Reticulatae Pericarpium* In some embodiments, the composition further comprises one or more herbs selected from the group consisting of *Polygonati odorati Rhizoma, Dioscoreae Rhizoma, Puerariae lobatae Radix, Poria*, and *Mori Cortex*. In some embodiments, the composition comprises about 1-98% (w) *Cyclocarya paliurus* leaves, about 1-98% (w) *Citri Reticulatae Pericarpium* and about 1-98% (w) of one or more herbs selected from the group consisting of *Polygonati odorati Rhizoma, Dioscoreae Rhizoma, Puerariae lobatae Radix, Poria*, and *Mori Cortex*. In some embodiments, the composition comprises about 10-80% (w) *Cyclocarya paliurus* leaves, about 10-80% (w) *Citri Reticulatae Pericarpium* and about 10-80% (w) of one or more herbs selected from the group consisting of *Polygonati odorati Rhizoma, Dioscoreae Rhizoma, Puerariae lobatae Radix, Poria*, and *Mori Cortex*. In some embodiments, the composition comprises about 20-60% (w) *Cyclocarya paliurus* leaves, about 20-60% (w) *Citri Reticulatae Pericarpium* and about 20-60% (w) of one or more herbs selected from the group consisting of *Polygonati odorati Rhizoma, Dioscoreae Rhizoma, Puerariae lobatae Radix, Poria*, and *Mori Cortex*. In some embodiments, the composition further comprises one or more herbs selected from the group consisting of *Lycii Fructus, Ginseng Radix et Rhizoma, Dendrobii Caulis, Angelicae sinensis Radix*, and *Rhodiolae Crenulatae Radix et Rhizoma*. In some embodiments, the composition further comprises one or more herbs selected from the group consisting of *Polygonati odorati Rhizoma, Dioscoreae Rhizoma, Puerariae lobatae Radix, Poria*, and *Mori Cortex*, and one or more herbs selected from the group consisting of *Lycii Fructus, Ginseng Radix et Rhizoma, Dendrobii Caulis, Angelicae sinensis Radix*, and *Rhodiolae Crenulatae Radix et Rhizoma*. In some of these embodiments, the composition comprises about 10-40% (w), about 20-30% (w), or about 25% (w) of one or more herbs selected from the group consisting of *Lycii Fructus, Ginseng Radix et Rhizoma, Dendrobii Caulis, Angelicae sinensis Radix*, and *Rhodiolae Crenulatae Radix et Rhizoma*. In some embodiments of any of the compositions, the composition further comprises one or more herbs selected from the group consisting of *Polygonati Rhizoma, Laminariae Thallus/Eckloniae Thallus, Mume Fructus, Notoginseng Radix et Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix*, Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition (e.g., a pharmaceutical composition or a nutritional composition) comprises (including consists essentially of or consists of) *Cyclocarya paliurus* leaves, *Mori Cortex* and *Dendrobii Caulis*. In some embodiments, the composition comprises about 20-60% (w) *Cyclocarya paliurus* leaves, about 20-60% (w) *Mori Cortex* and about 20-60% (w) *Dendrobii Caulis*. In some embodiments, the health care composition consists essentially of *Cyclocarya paliurus* leaves, *Mori Cortex* and *Dendrobii Caulis*. In some embodiments, the composition further comprises one or more herbs selected from the group consisting of *Polygonati odorati Rhizoma, Dioscoreae Rhizoma, Lycii Fructus, Ginseng Radix et Rhizoma, Angelicae sinensis Radix, Puerariae lobatae Radix, Poria, Citri Reticulatae Pericarpium, Rhodiolae Crenulatae Radix et Rhizoma, Mori Folium*, Green Tea, and *Siraitiae Fructus*. In some embodiments, the composition further comprises *Polygonati odorati Rhizoma, Puerariae lobatae Radix, Citri Reticulatae Pericarpium, Mori Folium*, Green Tea, and *Siraitiae Fructus*. In some embodiments, the composition comprises about 20-30% (w) *Cyclocarya paliurus* leaves, about 20-30% (w) *Mori Cortex*, about 20-30% (w) *Dendrobii Caulis*, about 5-10% (w) *Polygonati odorati Rhizoma*, about 5-10% (w) *Puerariae lobatae Radix*, about 5-10% (w) *Citri Reticulatae Pericarpium*, about 5-10% (w) *Mori Folium*, about 5-10% (w) Green Tea, and about 5-10% (w) *Siraitiae Fructus*. In some embodiments, the composition comprises about 20% (w) *Cyclocarya paliurus* leaves, about 20% (w) *Mori Cortex*, about 20% (w) *Dendrobii Caulis*, about 5% (w) *Polygonati odorati Rhizoma*, about 5% (w) *Puerariae lobatae Radix*, about 5% (w) *Citri Reticulatae Pericarpium*, about 5% (w) *Mori Folium*, about 10% (w) Green Tea, and about 10% (w) *Siraitiae Fructus*. In some embodiments, the health care composition consists essentially of *Cyclocarya paliurus* leaves, *Mori Cortex, Dendrobii Caulis, Polygonati odorati Rhizoma, Puerariae lobatae Radix, Citri Reticulatae Pericarpium, Mori Folium*, Green Tea, and *Siraitiae Fructus*. In some embodiments of any of the compositions, the composition further comprises one or more herbs selected from the group consisting of *Polygonati Rhizoma, Laminariae Thallus/Eckloniae Thallus, Mume Fructus, Notoginseng Radix et Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix*, Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyl-*

*lum*, Balsam pear, *Fagopyrum tataricum*, Pumpkin, Konjac, Celery, Corn Stigma, *Tremella, Hericium erinaceus*, and Garlic.

The invention also provides other health care compositions (e.g., a pharmaceutical composition or a nutritional composition) comprising (including consisting essentially of or consisting of) two or more herbs selected from the group consisting of *Mori Cortex, Dendrobii Caulis, Citri Reticulatae Pericarpium, Puerariae lobatae Radix* and *Polygonati odorati Rhizoma*, optionally the composition may further comprise one or more herbs selected from the group consisting of *Cyclocarya paliurus* leaves, *Dioscoreae Rhizoma, Poria, Lycii Fructus, Angelicae sinensis Radix, Ginseng Radix* et *Rhizoma* and *Rhodiolae Crenulatae Radix* et *Rhizoma*. The composition may be an oral formulation such as a tablet, a capsule, a granule, a powder, an effervescent tablet, or an herbal tea formulation, useful in lowering blood sugar, treating a disease or condition (e.g., diabetes, hyperglycemia, hypertension or hyperlipidemia), or providing nutritional supplement, to an individual in need thereof. These compositions can be made using methods and processes known in the art and those described herein.

In one embodiment, the health care composition (e.g., a pharmaceutical composition or a nutritional composition) comprises (including consists essentially of or consists of) *Mori Cortex* and *Dendrobii Caulis*. In some embodiments, the composition comprises about 1-99% (w) *Mori Cortex* and about 1-99% (w) *Dendrobii Caulis*. In some embodiments, the composition comprises about 20-80% (w) *Mori Cortex* and about 20-80% (w) *Dendrobii Caulis*. In some embodiments, the composition comprises about 30-70% (w) *Mori Cortex* and about 30-70% (w) *Dendrobii Caulis*. In some embodiments, the composition comprises about 40-60% (w) *Mori Cortex* and about 40-60% (w) *Dendrobii Caulis*. In some embodiments, the health care composition consists essentially of *Mori Cortex* and *Dendrobii Caulis*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 1-98% (w) *Mori Cortex*, about 1-98% (w) *Dendrobii Caulis* and about 1-98% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 10-80% (w) *Mori Cortex*, about 10-80% (w) *Dendrobii Caulis* and about 10-80% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 20-60% (w) *Mori Cortex*, about 20-60% (w) *Dendrobii Caulis* and about 20-60% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition further comprises one or more herbs selected from the group consisting of *Lycii Fructus, Ginseng Radix* et *Rhizoma, Citri Reticulatae Pericarpium, Angelicae sinensis Radix*, and *Rhodiolae Crenulatae Radix* et *Rhizoma*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves, and one or more herbs selected from the group consisting of *Lycii Fructus, Ginseng Radix* et *Rhizoma, Citri Reticulatae Pericarpium, Angelicae sinensis Radix*, and *Rhodiolae Crenulatae Radix* et *Rhizoma*. In some of these embodiments, the composition comprises about 10-40% (w), about 20-30% (w), or about 25% (w) of one or more herbs selected from the group consisting of *Lycii Fructus, Ginseng Radix* et *Rhizoma, Citri Reticulatae Pericarpium, Angelicae sinensis Radix*, and *Rhodiolae Crenulatae Radix* et *Rhizoma*. In some embodiments of any of the compositions, the composition further comprises one or more herbs selected from the group consisting of *Polygonati Rhizoma, Laminariae Thallus/Eckloniae Thallus, Mume Fructus, Notoginseng Radix* et *Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix*, Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition (e.g., a pharmaceutical composition or a nutritional composition) comprises (including consists essentially of or consists of) *Mori Cortex* and *Citri Reticulatae Pericarpium*. In some embodiments, the composition comprises about 1-99% (w) *Mori Cortex* and about 1-99% (w) *Citri Reticulatae Pericarpium*. In some embodiments, the composition comprises about 20-80% (w) *Mori Cortex* and about 20-80% (w) *Citri Reticulatae Pericarpium*. In some embodiments, the composition comprises about 30-70% (w) *Mori Cortex* and about 30-70% (w) *Citri Reticulatae Pericarpium*. In some embodiments, the composition comprises about 40-60% (w) *Mori Cortex* and about 40-60% (w) *Citri Reticulatae Pericarpium*. In some embodiments, the health care composition consists essentially of *Mori Cortex* and *Citri Reticulatae Pericarpium*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 1-98% (w) *Mori Cortex*, about 1-98% (w) *Citri Reticulatae Pericarpium* and about 1-98% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 10-80% (w) *Mori Cortex*, about 10-80% (w) *Citri Reticulatae Pericarpium* and about 10-80% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 20-60% (w) *Mori Cortex*, about 20-60% (w) *Citri Reticulatae Pericarpium* and about 20-60% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition further comprises one or more herbs selected from the group consisting of *Lycii Fructus, Ginseng Radix* et *Rhizoma, Dendrobii Caulis, Angelicae sinensis Radix*, and *Rhodiolae Crenulatae Radix* et *Rhizoma*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves, and one or more herbs selected from the group consisting of *Lycii Fructus, Ginseng Radix* et *Rhizoma, Dendrobii Caulis, Angelicae sinensis Radix*, and

*Rhodiolae Crenulatae Radix* et *Rhizoma*. In some of these embodiments, the composition comprises about 10-40% (w), about 20-30% (w), or about 25% (w) of one or more herbs selected from the group consisting of *Lycii Fructus, Ginseng Radix* et *Rhizoma, Dendrobii Caulis, Angelicae sinensis Radix*, and *Rhodiolae Crenulatae Radix* et *Rhizoma*. In some embodiments of any of the compositions, the composition further comprises one or more herbs selected from the group consisting of *Polygonati Rhizoma, Laminariae Thallus/Eckloniae Thallus, Mume Fructus, Notoginseng Radix* et *Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix,* Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition (e.g., a pharmaceutical composition or a nutritional composition) comprises (including consists essentially of or consists of) *Dendrobii Caulis* and *Citri Reticulatae Pericarpium*. In some embodiments, the composition comprises about 1-99% (w) *Dendrobii Caulis* and about 1-99% (w) *Citri Reticulatae Pericarpium*. In some embodiments, the composition comprises about 20-80% (w) *Dendrobii Caulis* and about 20-80% (w) *Citri Reticulatae Pericarpium*. In some embodiments, the composition comprises about 30-70% (w) *Dendrobii Caulis* and about 30-70% (w) *Citri Reticulatae Pericarpium*. In some embodiments, the composition comprises about 40-60% (w) *Dendrobii Caulis* and about 40-60% (w) *Citri Reticulatae Pericarpium*. In some embodiments, the health care composition consists essentially of *Dendrobii Caulis* and *Citri Reticulatae Pericarpium*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 1-98% (w) *Dendrobii Caulis*, about 1-98% (w) *Citri Reticulatae Pericarpium* and about 1-98% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 10-80% (w) *Dendrobii Caulis*, about 10-80% (w) *Citri Reticulatae Pericarpium* and about 10-80% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition comprises about 20-60% (w) *Dendrobii Caulis*, about 20-60% (w) *Citri Reticulatae Pericarpium* and about 20-60% (w) of one or more herbs selected from the group consisting of *Polygonati odorati Rhizoma, Dioscoreae Rhizoma, Puerariae lobatae Radix, Poria*, and *Cyclocarya paliurus* leaves. In some embodiments, the composition further comprises one or more herbs selected from the group consisting of *Lycii Fructus, Ginseng Radix* et *Rhizoma, Mori Cortex, Angelicae sinensis Radix*, and *Rhodiolae Crenulatae Radix* et *Rhizoma*. In some embodiments, the composition further comprises one or more herbs selected from the group consisting of *Polygonati odorati Rhizoma, Dioscoreae Rhizoma, Puerariae lobatae Radix, Poria*, and *Cyclocarya paliurus* leaves, and one or more herbs selected from the group consisting of *Lycii Fructus, Ginseng Radix* et *Rhizoma, Mori Cortex, Angelicae sinensis Radix*, and *Rhodiolae Crenulatae Radix* et *Rhizoma*. In some of these embodiments, the composition comprises about 10-40% (w), about 20-30% (w), or about 25% (w) of one or more herbs selected from the group consisting of *Lycii Fructus, Ginseng Radix* et *Rhizoma, Mori Cortex, Angelicae sinensis Radix*, and *Rhodiolae Crenulatae Radix* et *Rhizoma*. In some embodiments of any of the compositions, the composition further comprises one or more herbs selected from the group consisting of *Polygonati Rhizoma, Laminariae Thallus/Eckloniae Thallus, Mume Fructus, Notoginseng Radix* et *Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix,* Aloe, *Schisandrae chinensis Fructus, Ophiopogonis Radix*, Prepared Rhubarb, *Anemarrhenae Rhizoma, Tribuli Fructus, Ginkgo Folium, Astragali Radix, Gynostemma pentaphyllum*, Balsam pear, *Fagopyrum tataricum*, Pumpkin, Konjac, Celery, Corn Stigma, *Tremella, Hericium erinaceus*, and Garlic.

In one embodiment, the health care composition (e.g., a pharmaceutical composition or a nutritional composition) comprises (including consists essentially of or consists of) *Puerariae lobatae Radix* and *Dendrobii Caulis*. In some embodiments, the composition comprises about 1-99% (w) *Puerariae lobatae Radix* and about 1-99% (w) *Dendrobii Caulis*. In some embodiments, the composition comprises about 20-80% (w) *Puerariae lobatae Radix* and about 20-80% (w) *Dendrobii Caulis*. In some embodiments, the composition comprises about 30-70% (w) *Puerariae lobatae Radix* and about 30-70% (w) *Dendrobii Caulis*. In some embodiments, the composition comprises about 40-60% (w) *Puerariae lobatae Radix* and about 40-60% *Dendrobii Caulis* (w). In some embodiments, the health care composition consists essentially of *Puerariae lobatae Radix* and *Dendrobii Caulis*. In some embodiments, the composition further comprises one or more herbs selected from the group consisting of *Polygonati odorati Rhizoma, Dioscoreae Rhizoma, Mori Cortex, Poria*, and *Cyclocarya paliurus* leaves. In some embodiments, the composition comprises about 1-98% (w) *Puerariae lobatae Radix*, about 1-98% (w) *Dendrobii Caulis* and about 1-98% (w) of one or more herbs selected from the group consisting of *Polygonati odorati Rhizoma, Dioscoreae Rhizoma, Mori Cortex, Poria*, and *Cyclocarya paliurus* leaves. In some embodiments, the composition comprises about 10-80% (w) *Puerariae lobatae Radix*, about 10-80% (w) *Dendrobii Caulis* and about 10-80% (w) of one or more herbs selected from the group consisting of *Polygonati odorati Rhizoma, Dioscoreae Rhizoma, Mori Cortex, Poria*, and *Cyclocarya paliurus* leaves. In some embodiments, the composition comprises about 20-60% (w) *Puerariae lobatae Radix*, about 20-60% (w) *Dendrobii Caulis* and about 20-60% (w) of one or more herbs selected from the group consisting of *Polygonati odorati Rhizoma, Dioscoreae Rhizoma, Mori Cortex, Poria*, and *Cyclocarya paliurus* leaves. In some embodiments, the composition further comprises one or more herbs selected from the group consisting of *Lycii Fructus, Ginseng Radix* et *Rhizoma, Citri Reticulatae Pericarpium, Angelicae sinensis Radix*, and *Rhodiolae Crenulatae Radix* et *Rhizoma*. In some embodiments, the composition further comprises one or more herbs selected from the group consisting of *Polygonati odorati Rhizoma, Dioscoreae Rhizoma, Mori Cortex, Poria*, and *Cyclocarya paliurus* leaves, and one or more herbs selected from the group consisting of *Lycii Fructus, Ginseng Radix* et *Rhizoma, Citri Reticulatae Pericarpium, Angelicae sinensis Radix*, and *Rhodiolae Crenulatae Radix* et *Rhizoma*. In some of these embodiments, the composition comprises about 10-40% (w), about 20-30% (w), or about 25% (w) of one or more herbs selected from the group consisting of *Lycii Fructus, Ginseng Radix* et *Rhizoma, Citri Reticulatae Pericarpium, Angelicae sinensis Radix,* and *Rhodiolae Crenulatae Radix* et *Rhizoma.* In some embodiments of any of the compositions, the composition further comprises one or more herbs selected from the group consisting of *Polygonati Rhizoma, Laminariae Thallus/Eckloniae Thallus, Mume Fructus, Notoginseng Radix* et *Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix,* Aloe, *Schisandrae chinensis Fructus, Ophiopogonis Radix,* Prepared Rhubarb, *Anemarrhenae Rhizoma, Tribuli Fructus, Ginkgo Folium, Astragali Radix, Gynostemma pentaphyllum,* Balsam pear, *Fagopyrum tataricum,* Pumpkin, Konjac, Celery, Corn Stigma, *Tremella, Hericium erinaceus,* and Garlic.

In one embodiment, the health care composition (e.g., a pharmaceutical composition or a nutritional composition) comprises (including consists essentially of or consists of) *Mori Cortex* and *Polygonati odorati Rhizoma.* In some embodiments, the composition comprises about 1-99% (w) *Mori Cortex* and about 1-99% (w) *Polygonati odorati Rhizoma.* In some embodiments, the composition comprises about 20-80% (w) *Mori Cortex* and about 20-80% (w) *Polygonati odorati Rhizoma.* In some embodiments, the composition comprises about 30-70% (w) *Mori Cortex* and about 30-70% (w) *Polygonati odorati Rhizoma.* In some embodiments, the composition comprises about 40-60% (w) *Mori Cortex* and about 40-60% (w) *Polygonati odorati Rhizoma.* In some embodiments, the health care composition consists essentially of *Mori Cortex* and *Polygonati odorati Rhizoma.* In some embodiments, the composition further comprises one or more herbs selected from the group consisting of *Ginseng Radix* et *Rhizoma, Dioscoreae Rhizoma, Puerariae lobatae Radix, Poria,* and *Cyclocarya paliurus* leaves. In some embodiments, the composition comprises about 1-98% (w) *Mori Cortex,* about 1-98% (w) *Polygonati odorati Rhizoma* and about 1-98% (w) of one or more herbs selected from the group consisting of *Ginseng Radix* et *Rhizoma, Dioscoreae Rhizoma, Puerariae lobatae Radix, Poria,* and *Cyclocarya paliurus* leaves. In some embodiments, the composition comprises about 10-80% (w) *Mori Cortex,* about 10-80% (w) *Polygonati odorati Rhizoma* and about 10-80% (w) of one or more herbs selected from the group consisting of *Ginseng Radix* et *Rhizoma, Dioscoreae Rhizoma, Puerariae lobatae Radix, Poria,* and *Cyclocarya paliurus* leaves. In some embodiments, the composition comprises about 20-60% (w) *Mori Cortex,* about 20-60% (w) *Polygonati odorati Rhizoma* and about 20-60% (w) of one or more herbs selected from the group consisting of *Ginseng Radix* et *Rhizoma, Dioscoreae Rhizoma, Puerariae lobatae Radix, Poria,* and *Cyclocarya paliurus* leaves. In some embodiments, the composition further comprises one or more herbs selected from the group consisting of *Lycii Fructus, Dendrobii Caulis, Citri Reticulatae Pericarpium, Angelicae sinensis Radix,* and *Rhodiolae Crenulatae Radix* et *Rhizoma.* In some embodiments, the composition further comprises one or more herbs selected from the group consisting of *Ginseng Radix* et *Rhizoma, Dioscoreae Rhizoma, Puerariae lobatae Radix, Poria,* and *Cyclocarya paliurus* leaves, and one or more herbs selected from the group consisting of *Lycii Fructus, Dendrobii Caulis, Citri Reticulatae Pericarpium, Angelicae sinensis Radix,* and *Rhodiolae Crenulatae Radix* et *Rhizoma.* In some of these embodiments, the composition comprises about 10-40% (w), about 20-30% (w), or about 25% (w) of one or more herbs selected from the group consisting of *Lycii Fructus, Dendrobii Caulis, Citri Reticulatae Pericarpium, Angelicae sinensis Radix,* and *Rhodiolae Crenulatae Radix* et *Rhizoma.* In some embodiments of any of the compositions, the composition further comprises one or more herbs selected from the group consisting of *Polygonati Rhizoma, Laminariae Thallus/Eckloniae Thallus, Mume Fructus, Notoginseng Radix* et *Rhizoma, Ligustri lucidi Fructus, Corni Fructus, Chuanxiong Rhizoma, Atractylodis Rhizoma, Scrophulariae Radix, Rehmanniae Radix, Paeoniae Radix alba, Panacis Quinquefolii Radix,* Aloe, *Schisandrae chinensis Fructus, Ophiopogonis Radix,* Prepared Rhubarb, *Anemarrhenae Rhizoma, Tribuli Fructus, Ginkgo Folium, Astragali Radix, Gynostemma pentaphyllum,* Balsam pear, *Fagopyrum tataricum,* Pumpkin, Konjac, Celery, Corn Stigma, *Tremella, Hericium erinaceus,* and Garlic.

The health care composition may be an oral formulation such as a tablet, a capsule, a granule, a powder, an effervescent tablet, or an herbal tea formulation. The health care composition (such as a pharmaceutical composition or a nutritional composition) may further comprise one or more excipients. Examples of pharmaceutically acceptable excipient include but are not limited to pregelatinized starch, β-cyclodextrin, maltodextrin, Carbopol, microcrystalline cellulose, hydroxypropylmethylcellulose, low-substituted hydroxypropylcellulose, polyethylene glycol (PEG), sodium carboxymethyl cellulose, methylcellulose, ethylcellulose, mannitol, cross-linked sodium carboxymethyl cellulose, lactose, polyvinylpyrrolidone (PVP), magnesium stearate, talc, silica powder, aspartame, sodium bicarbonate, and sodium carbonate.

The health care compositions (such as a pharmaceutical composition or a nutritional composition) comprising the herbs (e.g., a Chinese herbal medicine) described herein may be prepared by methods known in the art, and methods described herein. For example, an herbal tea composition comprising one or more of the herbs described herein can be prepared by crushing and sieving the herbs, and packaging into a packet (e.g., a tea bag).

A granule composition can be prepared by extracting the herbs with a solvent (e.g., hot water) and converting the extracts into granules by using auxiliary agents or excipients such as β-cyclodextrin, microcrystalline cellulose, calcium hydrogen phosphate, or mannitol. A gel capsule composition can be manufactured by enclosure of a granule composition into a gel capsule. An herbal extract composition can be prepared by extracting the herbs, and removing impurities, for example, by filtration and centrifugation. Powders, oral tablets and effervescent tablets can be prepared using the herbal extracts and appropriate auxiliary materials by processes known in the art.

Herbal Extract Compositions and Methods of Making Thereof

One aspect of the invention provides an herbal extract composition (such as a pharmaceutical composition or a nutritional composition) comprising (including consisting essentially of or consisting of) an extract from a mixture of herbs known in Traditional Chinese Medicine, for example, *Cyclocarya paliurus* leaves and one, two or three herbs selected from the group consisting of *Mori Cortex, Dendrobii Caulis* and *Citri Reticulatae Pericarpium.* A method for preparing the herbal extract composition is further provided herein. The herbal extract composition disclosed herein comprising extracts from the herbs may provide synergistic effect in lowering blood sugar, while avoiding excessive toxicity often associated with long-term usage of Traditional Chinese Medicine due to factors such as heavy metal contamination and impurities. The herbal extract composition and its derivatives in the form of a gel capsule, a pharmaceutical composition, or a nutritional composition, used alone or in conjunction with standard anti-diabetic medication, can be a sustainable, cost-effective, and useful therapy for patients with diabetes, hyperglycemia, hypertension and/or hyperlipidemia, or people with other health conditions in need of lowering their blood sugar.

The present invention provides a method for preparing an herbal extract composition comprising (including consisting essentially of or consisting of) an extract of *Cyclocarya paliurus* leaves, *Mori. Cortex, Dendrobii Caulis* and *Citri Reticulatae Pericarpium*. The method may comprise the following steps:
  i) providing a mixture of *Cyclocarya paliurus* leaves, *Mori Cortex, Dendrobii Caulis* and *Citri Reticulatae Pericarpium*;
  ii) extracting said mixture with water (e.g., boiling water) to obtain an aqueous extract;
  iii) concentrating the aqueous extract to obtain a concentrated mixture;
  iv) obtaining a liquid portion of said concentrated mixture; and
  v) drying (e.g., spray-drying) said extract to produce the herbal extract composition.

In some embodiments, the method further comprises mixing the extract with an excipient (e.g., β-cyclodextrin, maltodextrin, or lactose) before drying.

The present invention provides an herbal extract composition prepared by the method described herein. The herbal extract composition comprises an extract of *Cyclocarya paliurus* leaves, *Mori Cortex, Dendrobii Caulis* and *Citri Reticulatae Pericarpium*. In some embodiments, the herbal extract composition consists essentially of or consists of an extract from a mixture of four herbal components: *Cyclocarya paliurus* leaves, *Mori Cortex, Dendrobii Caulis* and *Citri Reticulatae Pericarpium*.

The relative proportion of *Cyclocarya paliurus* leaves, *Mori Cortex, Dendrobii Caulis* and *Citri Reticulatae Pericarpium* in the herbal extract composition can be important for achieving optimal health benefits. In some embodiments, in the mixture of the four herbal components used to prepare the herbal extract composition, the relative ratio (by weight) of *Cyclocarya paliurus* leaves to *Mori Cortex* is about 1:4 to about 1:3, about 1:3 to about 1:2, about 1:3 to about 1:1, about 1:1 to about 2:1, about 2:1 to about 3:1, about 3:1 to about 4:1, about 1.2:1 to about 1:1.2, or preferably about 1:1. In some embodiments, the relative ratio (by weight) of *Cyclocarya paliurus* leaves to *Dendrobii Caulis* is about 1:4 to about 1:3, about 1:3 to about 1:2, about 1:3 to about 1:1, about 1:1 to about 2:1, about 2:1 to about 3:1, about 3:1 to about 4:1, about 3.5:2 to about 2.5:2, or preferably about 3:2. In some embodiments, the relative ratio (by weight) of *Cyclocarya paliurus* leaves to *Citri Reticulatae Pericarpium* is about any of about 1:3 to about 1:2, about 1:2 to about 1:1, about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 3.5:1 to about 2.5 to 1, or preferably about 3:1. In an exemplary embodiment, the herbal extract composition comprises (including consists essentially of or consists of) an extract from a mixture of *Cyclocarya paliurus* leaves, *Mori Cortex, Dendrobii Caulis* and *Citri Reticulatae Pericarpium*, wherein the mixture comprises (including consists essentially of or consists of) *Cyclocarya paliurus* leaves, *Mori Cortex, Dendrobii Caulis* and *Citri Reticulatae Pericarpium* in a relative proportion (by weight) of about 35:35:20:10, respectively. In some embodiments, provided is an herbal extract composition comprising an extract of *Cyclocarya paliurus* leaves, *Mori Cortex* (mulberry bark), *Dendrobii Caulis* and *Citri Reticulatae Pericarpium* (dried tangerine peel) at a relative proportion (by weight) of about 1-97%: 1-97%:1-97%:1-97%, about 10-70%:10-70%:10-70%:10-70%, about 30-40%:30-40%:10-30%:10-30%, or about 35%:35%:20%:10%, respectively.

In some embodiments, in the mixture of the four herbal components used to prepare the herbal extract composition, the percentage by weight of *Cyclocarya paliurus* leaves is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 25%-40%, or preferably about 33.3%. In some embodiments, the percentage by weight of *Mori Cortex* is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 25%-40%, or preferably about 33.3%. In some embodiments, the percentage by weight of *Dendrobii Caulis* is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, 15%-30%, or preferably about 22.2%. In some embodiments, the percentage by weight of *Citri Reticulatae Pericarpium* is about 1%-10%, 5%-15%, 10%-20%, 15%-25%, 20%-30%, 25%-35%, 30%-40%, 35%-40%, 40%-50%, 45%-55%, 50%-60%, 55%-65%, 60%-70%, 65%-75%, 70%-80%, 75-85%, 80%-90%, 85%-95%, 90-95%, 1%-40%, 40%-70%, 70%-95%, or preferably about 11.1%. In an exemplary embodiment, the herbal extract composition comprises an extract from an herbal mixture, wherein the mixture comprises (including consisting essentially of or consisting of) about 33.3% by weight of *Cyclocarya paliurus* leaves, about 33.3% by weight of *Mori Cortex*, about 22.2% by weight of *Dendrobii Caulis*, and about 11.1% by weight of *Citri Reticulatae Pericarpium*.

In a preferred embodiment of the present invention, in step i) of the method for preparing the herbal extract composition, for each about 1 portion (by weight) of *Citri Reticulatae Pericarpium*, about 3 portions (by weight) of *Cyclocarya paliurus* leaves, about 3 portions (by weight) of *Mori Cortex*, and about 2 portions (by weight) of *Dendrobii Caulis* are provided. In a particular embodiment, about 525 grams of *Cyclocarya paliurus* leaves, about 525 grams of *Mori Cortex*, about 300 grams of *Dendrobii Caulis* and about 150 grams of *Citri Reticulatae Pericarpium* are provided. The relative proportion of individual components within the compositions can be reasonably adjusted by persons skilled in the art according to actual production situation. In some embodiments, the mixture of crude herbs comprising (including consisting essentially of or consisting of) *Cyclocarya paliurus* leaves, *Mori Cortex, Dendrobii Caulis*, and *Citri Reticulatae Pericarpium* are optionally washed with potable water for multiple times (e.g. 3 times), or washed under running tap water for about any of 1 minute, 2 minutes, 5 minutes, or more than 5 minutes, to remove impurities, which may contain toxic substances and/or heavy metals. In some embodiments, potassium carbonate can optionally be added to the washed mixture of herbs, which may further reduce heavy metal contents in the herbal extract composition.

The extraction step ii) in the method for preparing the herbal extract composition can comprise one aqueous extraction step, two aqueous extraction steps, or more than two aqueous extraction steps, and the aqueous extracts obtained from the different extraction steps can be combined. One embodiment of the present invention provides a two-step extraction, which comprises extracting the mixture of *Cyclocarya paliurus* leaves, *Mori Cortex*, *Dendrobii Caulis* and *Citri Reticulatae Pericarpium* with a first portion of water to obtain a first aqueous extract; extracting the mixture again with a second portion of water to obtain a second aqueous extract; and combining the first and second aqueous extracts to give the aqueous extract ready for the later steps of the method. In particular, the water used in the extraction step(s) can be boiling water (at or above 100° C.), or hot water with a temperature higher than 37° C. and lower than 100° C. Alternatively, the extraction mixture can be boiled in water to provide the boiling water in any of the extraction steps.

The duration of the individual aqueous extraction steps can be optimized and determined by persons skilled in the art. For example, each aqueous extraction step can take about any of 1, 2, 3, 4, 5, 6, 7, 8, 9, 10, 11, or 12 hours. In a preferred embodiment of the two-step extraction step of the method, the duration of the first extraction step is about 2 hours, and the duration of the second extraction step is about 1 hour. In another embodiment, the duration of the first extraction step is more than about 2 hours but less than about 12 hours, and the duration of the second extraction step is more than about 1 hour but less than about 6 hours.

The amount of water used in the extraction steps can be about any of 1 time, 2 times, 3 times, 4 times, 5 times, 6 times, 7 times, 8 times, 9 times, 10 times, 11 times, 12 times, 13 times, 14 times, or more than 14 times by weight of the mixture of *Cyclocarya paliurus* leaves, *Mori Cortex*, *Dendrobii Caulis* and *Citri Reticulatae Pericarpium* provided in step i) of the method. For example, in a preferred embodiment of the two-step extraction, the first portion of water is about 12 times by weight of the mixture of *Cyclocarya paliurus* leaves, *Mori Cortex*, *Dendrobii Caulis* and *Citri Reticulatae Pericarpium*, and the second portion of water is about 10 times by weight of the mixture of *Cyclocarya paliurus* leaves, *Mori Cortex*, *Dendrobii Caulis* and *Citri Reticulatae Pericarpium*. In another embodiment, the first portion of water is about 10-15 times by weight of the mixture of *Cyclocarya paliurus* leaves, *Mori Cortex*, *Dendrobii Caulis* and *Citri Reticulatae Pericarpium*. In another embodiment of the present invention, the second portion of water is about 8-12 times by weight of the mixture of *Cyclocarya paliurus* leaves, *Mori Cortex*, *Dendrobii Caulis* and *Citri Reticulatae Pericarpium*. A person skilled in the art can combine the amount of water in any of the embodiments described here according to actual production situation.

In some embodiments, an optional filtration step can accompany each of the individual extraction steps, wherein the extract is filtered through a mesh filter (e.g. 200-40 mesh, or preferably an 80-mesh filter) to remove insoluble particles, which may contain toxic substances and/or heavy metals. An 40-mesh filter has a pore size of about 420 μm, and a mesh filter has a pore size of about 74 μm. Any particles larger than the pore size will be discarded after the optional filtration step(s), and the filtrate(s) will be combined for further steps in the method.

In some embodiments, prior to the concentration step iii), the aqueous extract is filtered through a mesh (e.g. 200-40 mesh, or preferably 200-mesh) filter to obtain a filtrate to be applied in the concentration step. A 200-mesh filter has a pore size of about 74 μm, thereby effectively removes from the aqueous extract particles larger than about 74 μm, which can contain substances not useful for lowering blood sugar, or contain toxic substances causing undesirable side effects. In other embodiments of the filtration step, a 200-40 mesh filter (about 74-420 μm in pore size) can be used to remove large insoluble particles. In one embodiment, chitosan is optionally added to the filtered aqueous extract (e.g. about 1% by weight of the herbal mixture), and mixed, for example, for about 15 minutes. The mixture with chitosan is allowed to stand overnight, and then filtered through a mesh (e.g. 200-40 mesh, or preferably 200 mesh) filter to obtain a filtrate with reduced heavy metal contents for the concentration step iii). Alternatively, in another embodiment, chitosan is optionally added to the filtered aqueous extract (e.g. about 1% by weight of the herbal mixture), mixed for about 15 minutes, and centrifuged (e.g. at about 4000-8000 rpm, or 5000-7000 rpm, or preferably at about 5380 rpm, for about 15 minutes) to obtain a supernatant with reduced heavy metal contents for the concentration step iii).

In one preferred embodiment, the concentration step iii) comprises concentrating the aqueous extract by heating the aqueous extract at about 65~80° C. under a vacuum of about −0.06~−0.04 MPa to obtain a concentrated mixture having a relative density of about 1.05 (measured at about 60° C.). The vacuum pressure specified in this embodiment is measured with respect to the atmospheric pressure, which is about 0.10 MPa. Therefore, the absolute vacuum pressure in this embodiment is about 0.04-0.06 MPa. It should be pointed out that the temperature and vacuum pressure used in the concentration step can be adjusted by persons skilled in the art according to actual production situation. The relative density of the concentrated mixture is measured with respect to the density of water, which is about 1 g/mL. In another embodiment of the present invention, the relative density of the concentrated mixture can be about 1.02-1.08 when measured at about 60° C.

To further remove insoluble particles from the aqueous extract, step iv) of the method can comprise obtaining a liquid portion of the concentrated mixture by allowing the concentrated mixture to stand at about 4° C. for about 12 hours or longer and taking a liquid portion that excludes the precipitate. In one embodiments of step iv), the concentrated mixture is allowed to stand at about 2° C.-10° C. In other embodiments, the concentrated mixture is allowed to stand for about any of 4 hours, 6, hours, 8 hours, 10 hours, 12 hours, 16 hours, 20 hour, or 24 hours. The precipitate or small solid particles discarded in this step may contain additional substances that are toxic, or ineffective in reducing blood sugar. In one embodiment, the concentrated mixture after standing is further filtered through a mesh (e.g. 200-40 mesh, or preferably 200-mesh) filter to remove the solid particles. In some embodiments, the concentrated mixture is centrifuged (e.g. at about 4000-800 rpm, or about 5000-7000 rpm, or about 5380 rpm) for about any of 10 minutes, 15 minutes, 20 minutes, 25 minutes, 30 minutes, or longer than 30 minutes, or preferably about 15 minutes to further reduce the heavy metal contents prior to the drying step v) of the method.

In some embodiments, the extract from step iv) is mixed with an excipient, such as a pharmaceutically acceptable excipient (e.g., β-cyclodextrin, maltodextrin, or lactose). The for introducing the excipient (e.g., β-cyclodextrin, maltodextrin, or lactose) to the herbal extract composition comprises mixing the liquid portion from step iv) with the excipient (e.g., β-cyclodextrin, maltodextrin, or lactose) by heating the liquid portion with an amount of the excipient (e.g., β-cyclodextrin, maltodextrin, or lactose) to about 80° C. and stir-mixing to obtain an extract. The temperature in the mixing step can be adjusted according to actual situation. In some embodiments, the ratio (by weight) of the excipient (e.g., β-cyclodextrin, maltodextrin, or lactose) to the mixture of *Cyclocarya paliurus* leaves, *Mori Cortex, Dendrobii Caulis* and *Citri Reticulatae Pericarpium* is about 1:100 to about 1:50, about 1:50 to about 1:40, about 1:40 to about 1:30, about 1:30 to about 1:20, about 1:20 to about 1:10, or less than about 1:10, or about 1:22 to about 1:28, or preferably about 1:25. In one embodiment, the herbal extract composition is prepared from an extract of a mixture of *Cyclocarya paliurus* leaves, *Mori Cortex, Dendrobii Caulis*, and *Citri Reticulatae Pericarpium*, and adding the excipient (e.g., β-cyclodextrin, maltodextrin, or lactose), wherein the relative proportion (by weight) of *Cyclocarya paliurus* leaves, *Mori Cortex, Dendrobii Caulis, Citri Reticulatae Pericarpium*, and the excipient (e.g., β-cyclodextrin, maltodextrin, or lactose) is about 525:525:300:150:60. A preferred embodiment of the herbal extract composition prepared from a mixture of about 525 grams of *Cyclocarya paliurus* leaves, about 525 grams of *Mori Cortex*, about 300 grams of *Dendrobii Caulis* and about 150 grams of *Citri Reticulatae Pericarpium* has about 60 grams of β-cyclodextrin added as an auxiliary component.

The drying (e.g., spray-drying) step v) of the method for preparing the herbal extract composition in some embodiments of the present invention comprises spray-drying the mixed extract in a spray-drying chamber having an in-flow temperature at about 180° C.-200° C. and an out-flow temperature of about 80° C.-100° C. to produce the herbal extract composition. The in-flow and out-flow temperatures of this step can be further adjusted according to actual situation. Other suitable drying methods can also be used.

Finally, the method for preparing the herbal extract composition can further comprise packing and sealing the herbal extract composition in a sterile package. The sterile package can be a plastic package, a paper package, a nylon package or any package deemed suitable by persons skilled in the art. The herbal extract composition can be placed in a single-layered sterile package, or a double-layered sterile package.

Accordingly, an herbal extract composition prepared by any embodiment of the method detailed herein is provided by the present invention. Any of the steps and parameters described herein can be combined, as if each and every combination is individually described, to prepare the herbal extract composition comprising (including consisting essentially of or consisting of) an extract of *Cyclocarya paliurus* leaves, *Mori Cortex, Dendrobii Caulis* and *Citri Reticulatae Pericarpium*. Example 1 describes such an exemplary method and the herbal extract composition prepared by this method.

Because of the multiple-step preparation method, the herbal extract composition provided by the present invention is characterized by a low concentration of heavy metals and other toxic elements. Common heavy metals found in Chinese medicine compositions include manganese, copper, cadmium, lead, iron, mercury, zinc and arsenic. In some embodiments, the herbal extract composition detailed herein contains a total of about less than 20 ppm (parts per million), less than 15 ppm, less than 10 ppm, less than 5 ppm, less than 1 ppm, or less than 0.5 ppm of combined heavy metal content. In some embodiments, the herbal extract composition contains about less than 5 ppm, less than 2 ppm, less than 1 ppm, less than 0.5 ppm, or less than 0.1 ppm of lead; and/or about less than 3 ppm, less than 2 ppm, less than 1 ppm, less than 0.5 ppm, or less than 0.1 ppm of arsenic; and/or about less than 3 ppm, less than 2 ppm, less than 1 ppm, less than 0.5 ppm, or less than 0.1 ppm of mercury. The low level of heavy metals ensures safety for long-term human consumption of the herbal extract composition and its derived compositions and products.

The heavy metal contents in the crude herbs (e.g. *Cyclocarya paliurus* leaves, *Mori Cortex, Dendrobii Caulis* and *Citri Reticulatae Pericarpium*) that are used to prepare the herbal extract composition can vary significantly depending on their origins of production, thereby affecting the overall heavy metal contents of the herbal extract composition and its derivate products (e.g. pharmaceutical compositions, nutritional compositions, capsules and other forms of products comprising the herbal extract composition). Table 1 lists representative concentrations of lead and arsenic as measured using methods known in the art in crude *Cyclocarya paliurus* leaves, *Mori Cortex, Dendrobii Caulis* and *Citri Reticulatae Pericarpium* from various origins where the herbs are harvested and optionally methoded prior to their use in producing the herbal extract composition. To warrant a desirable heavy metal content, in some embodiments of the method for preparing the herbal extract composition, *Cyclocarya paliurus* leaves, *Mori Cortex, Dendrobii Caulis* and *Citri Reticulatae Pericarpium* from origins that are associated with low overall heavy metal contents, or low concentrations of particular heavy metals (such as lead and/or arsenic) as described herein are selected.

TABLE 1

Heavy metal contents in exemplary crude herbs from different origins

| Crude herbs | Origin in China | Lead (ppm) | Arsenic (ppm) |
|---|---|---|---|
| *Cyclocarya paliurus* leaves | Sui Ning, Hunan Province | 1.1 | 0.17 |
| | Shi En, Hubei Province | 1.4 | 0.15 |
| | Zhang Jia Jie, Hunan Province | 1.8 | 0.16 |
| | Huang Ao Xiang, Jiangxi Province | 1.7 | <0.5 |
| | Guan Shan, Jiangxi Province | 3.7 | 0.33 |
| | Da Lian Shan, Jiangxi Province | 2.3 | 0.27 |
| Mori Cortex | Sichuan Province | 0.21 | 0.23 |
| | Zhejiang Province | 0.28 | 0.13 |
| Dendrobii Caulis | N/A | <0.5 | <0.5 |
| Citri Reticulatae Pericarpium | Hebei Province | 0.25 | 0.11 |
| | Guangdong Province | 1.8 | 1.6 |

The herbal extract composition contains polysaccharides and/or flavonoids, which may be bioactive and have beneficial effects in lowering blood sugar. In some embodiments, the herbal extract composition contains about 3%-30%, about 5%-20%, or about 10%-15% of polysaccharides. In some embodiments, the herbal extract composition contains about 1%-15%, 2%-10%, or 3%-5% of flavonoids.

Besides the extract from the mixture of *Cyclocarya paliurus* leaves, *Mori Cortex, Dendrobii Caulis* and *Citri Reticulatae Pericarpium*, the herbal extract composition can contain additional components, such as auxiliary components, to ensure desirable physiochemical and biopharmaceutical properties, for example stability and bioaccessibility of active substances. In some embodiments, the percentage by weight of β-cyclodextrin in the herbal extract composition is about 0-20%, 1-5%, 5-10%, 0-20%, 15-25%, 20-30%, 25-35%, 30-40%, 35-40%, 40-50%, 45-55%, 1-15%, 15-30%, 30-50%, or preferably about 20%, about 19.5%, or about 19%.

The herbal extract composition disclosed in the present invention can be incorporated in a nutritional composition, which may further comprise dietary materials and carriers. Examples of dietary materials and carriers include, but are not limited to, starch, talc, magnesium stearate, powdered milk, vitamins, flavoring agents, preservatives, dyes, and combinations thereof.

Likewise, the herbal extract composition can be incorporated in a pharmaceutical composition comprising any embodiment of the herbal extract composition detailed herein and a pharmaceutically acceptable carrier. "Pharmaceutically acceptable carrier" refers to a solid or liquid filler or gelatin material which is compatible with the herbal extract composition, and is suitable to be used in human with sufficient purity and sufficiently low toxicity. Examples of pharmaceutically acceptable carrier include, but are not limited to, cellulose and its derivatives, gelatin, colorants, flavoring agents, stabilizers, and the like. In one embodiment of the present invention, the pharmaceutical composition comprises any of the herbal extract compositions detailed herein, microcrystalline cellulose and calcium hydrogen phosphate. In another embodiment, the pharmaceutical composition further comprises magnesium stearate.

In some embodiments, the ratio (by weight) of microcrystalline cellulose used in preparing of the pharmaceutical composition to the mixture of *Cyclocarya paliurus* leaves, *Mori Cortex, Dendrobii Caulis* and *Citri Reticulatae Pericarpium* used in preparing the herbal extract composition is about 1:200 to about 1:100, about 1:100 to about 1:75, about 1:75 to about 1:50, about 1:50 to about 1:25, about 1:25 to about 1:10, or less than about 1:10, about 1:45 to about 1:55, or preferably about 1:49.6. In some embodiments, the ratio (by weight) of calcium hydrogen phosphate used to the mixture of *Cyclocarya paliurus* leaves, *Mori Cortex, Dendrobii Caulis* and *Citri Reticulatae Pericarpium* used is about 1:200 to about 1:100, about 1:100 to about 1:75, about 1:75 to about 1:50, about 1:50 to about 1:25, about 1:25 to about 1:10, about 1:65 to about 1:75, or less than about 1:10, or preferably about 1:71.4. In some embodiments, the ratio (by weight) of magnesium stearate used to the mixture of *Cyclocarya paliurus* leaves, *Mori Cortex, Dendrobii Caulis* and *Citri Reticulatae Pericarpium* used is about 1:2000 to about 1:1500, about 1:1500 to about 1:1000, about 1:1000 to about 1:750, about 1:750 to about 1:500, about 1:500 to about 1:250, about 1:250 to about 1:100, or less than about 1:100, about 1:800 to about 1:900, or preferably about 1:857. In some embodiments, the percentage by weight of β-cyclodextrin in the pharmaceutical composition is about 0-20%, 1-5%, 5-10%, 0-20%, 15-25%, 20-30%, 25-35%, 30-40%, 35-40%, 40-50%, 45-55%, 1-15%, 15-30%, 30-50%, 15-20%, or preferably about 17.1%. In some embodiments, the percentage by weight of microcrystalline cellulose in the pharmaceutical composition is about 0-20%, 1-5%, 5-10%, 0-20%, 15-25%, 20-30%, 25-35%, 30-40%, 35-40%, 40-50%, 45-55%, 1-15%, 15-30%, 30-50%, 30-50%, or preferably about 8.6%. In some embodiments, the percentage by weight of calcium hydrogen phosphate in the pharmaceutical composition is about 0.1%-1%, 1-2%, 2-4%, 4-8%, 3-7%, 5-10%, 10-20%, 15-25%, 20-30%, 25-35%, 30-40%, 0.1-15%, 15-30%, or preferably about 6%. In some embodiments, the percentage by weight of magnesium stearate in the pharmaceutical composition is about 0.01-0.1%, 0.1-0.5%, 0.2-0.6%, 0.4-0.8%, 0.5-1%, 1-2%, 0.2-2%, 2-5%, 5-10%, or preferably about 0.5%. In one embodiment, the pharmaceutical composition is prepared from an extract of a mixture of *Cyclocarya paliurus* leaves, *Mori Cortex, Dendrobii Caulis*, and *Citri Reticulatae Pericarpium*, and adding β-cyclodextrin, microcrystalline cellulose, calcium hydrogen phosphate, and magnesium stearate, wherein the relative proportion (by weight) of *Cyclocarya paliurus* leaves, *Mori Cortex, Dendrobii Caulis, Citri Reticulatae Pericarpium*, β-cyclodextrin, microcrystalline cellulose, calcium hydrogen phosphate, and magnesium stearate is about 525:525:300:150:60:30.25:21:1.75. In a preferred embodiment, the pharmaceutical composition comprises an extract from a mixture of about 525 parts by weight (such as 525 grams) of *Cyclocarya paliurus* leaves, about 525 parts by weight (such as 525 grams) of *Mori Cortex*, about 300 parts by weight (such as 300 grams) of *Dendrobii Caulis* and about 150 parts by weight (such as 150 grams) of *Citri Reticulatae Pericarpium*, together with auxiliary components, including about 60 parts by weight (such as 60 grams) of β-cyclodextrin, about 30.25 parts by weight (such as 30.25 grams) grams of microcrystalline cellulose, about 21 parts by weight (such as 21 grams) of calcium hydrogen phosphate, and about 1.75 parts by weight (such as 1.75 grams) of magnesium stearate. The relative proportion of *Cyclocarya paliurus* leaves, *Mori Cortex, Dendrobii Caulis* and *Citri Reticulatae Pericarpium* and the various auxiliary components in any of the compositions detailed herein can be reasonably adjusted by persons skilled in the art according to actual production situation.

Herbal extract compositions comprising other combinations of herbs described herein can be prepared using the methods described herein with the desirable herbs. For example, an herbal extract composition comprising an extract of *Cyclocarya paliurus* leaves and one, two or three herbs selected from the group consisting of *Mori Cortex, Dendrobii Caulis* and *Citri Reticulatae Pericarpium* can be prepared using any one of the methods detailed herein for preparing an herbal extract composition using a mixture of *Cyclocarya paliurus* leaves and the one, two or three herbs selected from the group consisting of *Mori Cortex, Dendrobii Caulis* and *Citri Reticulatae Pericarpium*. An herbal extract composition comprising two or more herbs selected from the group consisting of *Mori Cortex, Dendrobii Caulis, Citri Reticulatae Pericarpium, Puerariae lobatae Radix* and *Polygonati odorati Rhizoma*, optionally comprising one or more herbs selected from the group consisting of *Cyclocarya paliurus* leaves, *Dioscoreae Rhizoma, Poria, Lycii Fructus, Angelicae sinensis Radix, Ginseng Radix et Rhizoma* and *Rhodiolae Crenulatae Radix et Rhizoma*, can be prepared using any one of the methods detailed herein for preparing an herbal extract composition using a mixture of the two or more herbs selected from the group consisting of *Mori Cortex, Dendrobii Caulis, Citri Reticulatae Pericarpium, Puerariae lobatae Radix* and *Polygonati odorati Rhizoma*, optionally the one or more herbs selected from the group consisting of *Cyclocarya paliurus* leaves, *Dioscoreae Rhizoma, Poria, Lycii Fructus, Angelicae sinensis Radix, Ginseng Radix et Rhizoma* and *Rhodiolae Crenulatae Radix et Rhizoma*.

The herbal extract composition, the nutritional composition, and the pharmaceutical composition detailed herein are useful in lowering blood sugar, treating a disease or condition (e.g., diabetes, hyperglycemia, hypertension or hyperlipidemia), or providing nutritional supplement, to an individual in need thereof. The herbal extract composition can be used in the manufacture of a medicament for lowering blood sugar, treating a disease or condition (e.g., diabetes, hyperglycemia, hypertension or hyperlipidemia), or providing nutritional supplement, to an individual in need thereof in a subject in need thereof. The compositions detailed herein can be administered in any suitable form via any route. A preferred route is oral administration.

Further provided is an oral formulation comprising a combination of herbs detailed herein. The oral formulation may be a tablet, a capsule, a granule, a powder, an effervescent tablet, or an herbal tea formulation. The oral formulations may be prepared from an herbal extract composition, a nutritional composition, or a pharmaceutical composition detailed herein.

Also provided is a method of preparing an oral formulation comprising one or more herbal components detailed herein, the method comprising mixing an herbal extract composition detailed herein with one or more pharmaceutically acceptable carrier or excipients. In some embodiments, the pharmaceutically acceptable excipients independently selected from the group consisting of pregelatinized starch, β-cyclodextrin, maltodextrin, Carbopol, microcrystalline cellulose, hydroxypropylmethylcellulose, low-substituted hydroxypropylcellulose, polyethylene glycol (PEG), sodium carboxymethyl cellulose, methylcellulose, ethylcellulose, mannitol, cross-linked sodium carboxymethyl cellulose, lactose, polyvinylpyrrolidone (PVP), magnesium stearate, talc, silica powder, aspartame, sodium bicarbonate, and sodium carbonate.

Gel Capsule and Methods of Making Gel Capsules

The present invention provides a method for preparing a gel capsule comprising an herbal extract composition described herein, a microcrystalline cellulose, and calcium hydrogen phosphate, wherein the method comprises the following steps:
1) mixing the herbal extract composition with a microcrystalline cellulose and calcium hydrogen phosphate to obtain a first mixture;
2) treating a portion of said first mixture with an alcoholic solvent to obtain a wet granule;
3) drying the wet granule to obtain a dry granule;
4) mixing said dry granule with magnesium stearate to obtain a second mixture; and
5) filling a portion of said second mixture in a gel capsule.

In one aspect, a method is provided for preparing a gel capsule comprising an herbal extract composition comprising (including consisting essentially of or consisting of) an extract of *Cyclocarya paliurus* leaves and one, two or three herbs selected from the group consisting of *Mori Cortex*, *Dendrobii Caulis* and *Citri Reticulatae Pericarpium*, as well as a microcrystalline cellulose and calcium hydrogen phosphate comprising steps 1)-5) of the preceding method, wherein the herbal extract composition is prepared by any one of the methods detailed herein for preparing an herbal extract composition.

In one embodiment, provided is a method for preparing a gel capsule comprising an herbal extract composition comprising (including consisting essentially of or consisting of) an extract of *Cyclocarya paliurus* leaves, *Mori Cortex*, *Dendrobii Caulis* and *Citri Reticulatae Pericarpium*, as well as a microcrystalline cellulose and calcium hydrogen phosphate. The method comprises steps 1)-5) of the preceding method, wherein the herbal extract composition is prepared by the method comprising:
i) providing a mixture of *Cyclocarya paliurus* leaves, *Mori Cortex*, *Dendrobii Caulis* and *Citri Reticulatae Pericarpium*;
ii) extracting said mixture with water (e.g., boiling water) to obtain an aqueous extract;
iii) concentrating the aqueous extract to obtain a concentrated mixture;
iv) obtaining a liquid portion of said concentrated mixture; and
v) drying (e.g., spray-drying) said extract to produce the herbal extract composition.

The relative proportion (by weight) of each initial ingredient provided to make the gel capsule can be important for optimum function of the gel capsule. In one embodiment of the present invention, a predetermined amount of the herbal extract composition, a predetermined amount of microcrystalline cellulose and a predetermined amount of calcium phosphate are first weighed to be used in the method for making the gel capsule. In an exemplary embodiment, the gel capsule is prepared from the herbal extract composition, which is prepared from an extract of a mixture of about 525 grams of *Cyclocarya paliurus* leaves, about 525 times weight (e.g. about 525 grams) of *Mori Cortex*, about 300 times weight (e.g. about 300 grams) of *Dendrobii Caulis*, and about 150 times weight (e.g. about 150 grams) of *Citri Reticulatae Pericarpium*, as well as about 60 times weight (e.g. about 60 grams) of 3-cyclodextrin, about 30.25 times weight (e.g. about 30.25 grams) of microcrystalline cellulose, about 21 times weight (e.g. about 21 grams) of calcium hydrogen phosphate, and about 1.75 times weight (or about 1.75 grams) of magnesium stearate. The relative amounts of the components, such as the herbal extract composition, β-cyclodextrin, microcrystalline cellulose, calcium hydrogen phosphate, and magnesium stearate, can be in any of the ratios described herein.

Several other parameters of the method for preparing the gel capsule can be important. Also, additional steps and modifications to the steps in the method can be helpful for optimization of the gel capsule. In one preferred embodiment, the first mixing step 1) of the method comprises mixing the herbal extract composition with a microcrystalline cellulose and calcium hydrogen phosphate for about 20 minutes to obtain a uniform mixture. The duration of this mixing step can be longer than 20 minutes to ensure desirable homogeneity.

The extraction step 1) of the method can be carried out in a multi-function extractor or another suitable apparatus or container. The alcoholic solvent used to treat the first mixture in step 2) can be 95% ethanol in aqueous solution, or other alcohols and alcoholic solutions of comparable extraction capacity and properties that are commonly used in food production. In order to screen for granules of appropriate size, step 2) of the method can further comprise a step of sieving the wet granule through a sieve, such as a 20-mesh sieve, prior to drying the granule. A 20-mesh sieve has a pore size of about 0.841 mm, thereby allowing wet granule with a size smaller than about 0.841 mm to be selected for further methoding into the gel capsule. A sieve of comparable pore size, such as a 25-mesh (about 0.707 mm pore size) to 18-mesh (about 1 mm pore size) sieve can be applied in this sieving step in some embodiments of the present invention.

One preferred set of conditions for drying the wet granule in step 4) of the method requires a temperature of about 65° C.-75° C. for drying, and the dry granule contains less than about 5% water. In some embodiments, the dry granule contains less than 4% water, less than 2% water, or less than 1% water. A sieving step for the dry granule can also be included in step 3), in which the dry granule is sieved through a 20-mesh sieve, or a sieve with comparable pore size to select for dry granules of appropriate size. In some embodiments, dry granule with a particle size smaller than 20-mesh, or about 0.841 mm, can be selected for further methoding.

In the mixing step 4) after drying, one preferred embodiment of the method comprises mixing the dry granule with magnesium stearate for about 10 minutes to obtain a second uniform mixture. The duration of mixing in step 5) can be longer than 10 minutes to obtain desirable homogeneity.

In the filling step 5) of the method, an empty gel capsule (e.g. a size 0 gel capsule, or a size 1 gel capsule) can be used to fill about 0.35 gram of the second mixture. A size 0 gel capsule can be a cylindrical two-piece gel capsule, having a volume of about 0.67 mL and a dimension of about 21.7 mm in locked length, and an external diameter of about 7.65 mm. Empty gel capsules of other sizes may be used, and the number of gel capsules administered to subjects in need can be adjusted accordingly to achieve the same therapeutic or nutritional regimen. Any suitable materials can be used for the shell of the gel capsules. Usually, the shell of a gel capsule is made of either gelatin derived from animal collagen extracts, or plant polysaccharides and their derivatives. Additional steps comprising polishing the gel capsule, packaging and testing for quality control can be included in the method for preparing the gel capsule according to production standards.

It is intended that any of the steps and parameters described herein for preparing the herbal extract compositions (for example, an herbal extract composition comprising (including consisting essentially of or consisting of) *Cyclocarya paliurus* leaves, *Mori Cortex*, *Dendrobii Caulis* and *Citri Reticulatae Pericarpium*) can be combined with any of the steps and parameters described herein for preparing the gel capsule, as if each and every combination is individually described. For example, in one embodiment, a gel capsule comprising an herbal extract composition comprising (including consisting essentially of or consisting of) *Cyclocarya paliurus* leaves, *Mori Cortex*, *Dendrobii Caulis*, *Citri Reticulatae Pericarpium* and β-cyclodextrin, which further comprises microcrystalline cellulose, calcium hydrogen phosphate, and magnesium stearate, is prepared by the method comprising weighing out a starting mixture of about 525 times weight (e.g. about 525 grams) of *Cyclocarya paliurus* leaves, about 525 times weight (e.g. about 525 grams) of *Mori Cortex*, about 300 times weight (e.g. about 300 grams) of *Dendrobii Caulis*, about 150 times weight (e.g. about 150 grams) of *Citri Reticulatae Pericarpium*; extracting said starting mixture with a first portion of about 12 times (by weight of said starting mixture) of boiling water for about 2 hours to obtain a first aqueous extract; further extracting said starting mixture with a second portion of about 10 times (by weight of said starting mixture) for about 1 hour to obtain a second aqueous extract; combining said first aqueous extract and said second aqueous extract to give a combined aqueous extract; filtering the combined aqueous extract through a 200-mesh filter to obtain a filtrate; concentrating the filtrate by heating the filtrate at about 65-80° C. under a vacuum of about −0.06~−0.04 MPa to obtain a concentrated mixture, wherein the concentrated mixture has a relative density of about 1.05 (measured at about 80° C.); allowing the concentrated mixture to stand at about 4° C. for about 12 hours or longer and taking a liquid portion of the concentrated mixture; optionally mixing said liquid portion with an excipient (e.g., β-cyclodextrin, maltodextrin, or lactose) by heating said liquid portion with about 60 times weight (e.g. about 60 grams) of the excipient (e.g., β-cyclodextrin, maltodextrin, or lactose) to about 80° C. and stir-mixing to obtain an extract; spray-drying said extract in a spray-drying chamber having an in-flow temperature at about 180° C.~200° C. and an out-flow temperature of about 80° C.~100° C. to produce an herbal extract composition; mixing said herbal extract composition with about 30.25 times weight (e.g. about 30.25 grams) of microcrystalline cellulose and about 21 times weight (e.g. about 21 grams) of calcium hydrogen phosphate for about 20 minutes to obtain a first uniform mixture; treating the first uniform mixture with 95% ethanol used for food production to obtain a wet granule; sieving the wet granule through a 20-mesh sieve to obtain a wet granule with particle size smaller than 20-mesh; drying the wet granule with particle size smaller than 20-mesh at about 67° C.~75° C. to obtain a dry granule, wherein the dry granule contains less than about 5% water; sieving the dry granule through a 20-mesh sieve to obtain a dry granule with particle size smaller than 20-mesh; mixing the dry granule with particle size smaller than 20-mesh with about 1.75 times weight (e.g. about 1.75 grams) of magnesium stearate for about 10 minutes to obtain a second uniform mixture; filling a portion of about 0.35 times weight (e.g. about 0.35 gram) of said second uniform mixture in a size 0 gel capsule to obtain a gel capsule; polishing the gel capsule; packaging the polished gel capsule; and testing the packaged gel capsule for quality control.

In another embodiment, a gel capsule comprising an herbal extract composition comprising (including consisting essentially of or consisting of) *Cyclocarya paliurus* leaves, *Mori Cortex*, *Dendrobii Caulis*, *Citri Reticulatae Pericarpium* and an excipient (e.g., β-cyclodextrin, maltodextrin, or lactose), which further comprises microcrystalline cellulose, calcium hydrogen phosphate, and magnesium stearate, is prepared by the method comprising weighing out a starting mixture of about 525 times weight (e.g. about 525 grams) of *Cyclocarya paliurus* leaves, about 525 times weight (e.g. about 525 grams) of *Mori Cortex*, about 300 times weight (e.g. about 300 grams) of *Dendrobii Caulis*, about times weight (e.g. about 150 grams) of *Citri Reticulatae Pericarpium*; optionally washing said starting mixture with water for 3 times; extracting said starting mixture with a first portion of about 12 times (by weight of said starting mixture, e.g. about 3.6 L) of boiling water for about 2 hours to obtain a first aqueous extract; optionally filtering the first aqueous extract through a mesh filter (e.g. 200-40 mesh, or preferably 80-mesh) to obtain a first filtered aqueous extract; further extracting said starting mixture with a second portion of about 10 times (by weight of said starting mixture, e.g. about 3 L) for about 1 hour to obtain a second aqueous extract; optionally filtering the second aqueous extract through a mesh filter (e.g. 200-40 mesh, or preferably 80-mesh) to obtain a second filtered aqueous extract; combining said first (filtered) aqueous extract and said second (filtered) aqueous extract to give a combined aqueous extract; optionally filtering said combined aqueous extract through a mesh (e.g. 200-40 mesh, or preferably 200-mesh) filter; concentrating the combined (filtered) aqueous extract (e.g. to about 2000 mL) to obtain a concentrated mixture; allowing the concentrated mixture to stand at about 4° C. for about 12 hours or longer and taking a first liquid portion of the concentrated mixture; optionally centrifuging said first liquid portion (e.g. for about 15 minutes) at about 4000-8000 rpm (e.g. 5380 rpm) and taking a second liquid portion of the centrifuged concentrated mixture; mixing said (first or second) liquid portion with an excipient (e.g., β-cyclodextrin, maltodextrin, or lactose) by heating said (first or second) liquid portion with about 60 times weight (e.g. about 60 grams) of the excipient (e.g., β-cyclodextrin, maltodextrin, or lactose) to about 80° C. and stir-mixing to obtain an extract; spray-drying said extract in a spray-drying chamber having an in-flow temperature at about 180° C.~200° C. and an out-flow temperature of about 80° C.~100° C. to produce an herbal extract composition; mixing said herbal extract composition with about 30.25 times weight (e.g. about 30.25 grams) of microcrystalline cellulose and about 21 times weight (e.g. about 21 grams) of calcium hydrogen phosphate for about 20 minutes to obtain a first uniform mixture; treating the first uniform mixture with 95% ethanol used for food production to obtain a wet granule; sieving the wet granule through a 20-mesh sieve to obtain a wet granule with particle size smaller than 20-mesh; drying the wet granule with particle size smaller than 20-mesh at about 67° C.~75° C. to obtain a dry granule, wherein the dry granule contains less than about 5% water; sieving the dry granule through a 20-mesh sieve to obtain a dry granule with particle size smaller than 20-mesh; mixing the dry granule with particle size smaller than 20-mesh with about 1.75 times weight (e.g. about 1.75 grams) of magnesium stearate for about 10 minutes to obtain a second uniform mixture; filling a portion of about 0.35 gram of said second uniform mixture in a size 0 oe aize 1 gel capsule to obtain a gel capsule; polishing the gel capsule; packaging the polished gel capsule; and testing the packaged gel capsule for quality control. The embodiment of the method described herein can prepare gel capsules with reduced heavy metal contents. Some of the other embodiments that can reduce heavy metal contents in the herbal extract composition, the herbal extract gel capsules, the nutritional composition, or the pharmaceutical composition are described in Examples 5-10.

Methods for Use

One aspect of the present invention provides a method of lowering blood sugar in a subject in need thereof comprising administering to the subject a therapeutically effective amount of an herbal extract composition, a gel capsule, a nutritional composition, or a pharmaceutical composition described herein, each independently, comprising (including consisting essentially of or consisting of) an extract of the herbal combinations detailed herein, for example, an herbal combination of *Cyclocarya paliurus* leaves and one, two or three herbs selected from the group consisting of *Mori Cortex, Dendrobii Caulis* and *Citri Reticulatae Pericarpium*, preferably, an herbal combination of *Cyclocarya paliurus* leaves, *Mori Cortex, Dendrobii Caulis* and *Citri Reticulatae Pericarpium*. The subject in need can be a human patient suffering from diabetes, other metabolic diseases, or other conditions associated with an elevated blood sugar level. Blood sugar refers to the variety of naturally occurring carbohydrates, including monosaccharides, oligosaccharides, and polysaccharides that are normally found in the blood stream, blood or any serological fraction of the blood, such as serum. One monosaccharide species, glucose, is the primary source of energy for cells in all organisms, and therefore, glucose is one of the most abundant and highly regulated sugars in the blood. In some but not all embodiments of the present invention, "lowering blood sugar" specifically refers to lowering blood glucose. Lowering of blood sugar levels is an effective strategy to treat and manage human conditions, such as diabetes and other metabolic conditions that are responsive to reduced blood sugar level. Therefore, the method described herein can also be applied to treat any disease or condition responsive to lowering of blood sugar. In some embodiments, provided is a method for treating hyperglycemia, hypertension and/or hyperlipidemia in an individual in need thereof.

Alternatively, the herbal extract composition, the gel capsule or the nutritional composition described herein can be used as a nutritional supplement in a method provided by the present invention to reduce blood sugar in a subject in need thereof. "Nutritional supplement" refers to substance that may have beneficial health effects, but are normally absent or present at insufficient quantities in a person's diet. As a nutritional supplement, the herbal extract composition, the gel capsule, or the nutritional composition should be administered to the subject in need thereof in conjunction with standard and other therapeutic means to help the subject manage his or her blood sugar levels.

"Therapeutically effective amount" or "effective amount" in the present invention refers to an amount of an herbal extract composition, a gel capsule, a nutritional composition, or a pharmaceutical composition sufficient to improve the condition of the subject in need thereof, without causing serious side-effects. In a preferred embodiment of the present invention, the gel capsules described in Examples 1 and 2 are administered orally with a dosage regimen of 2 doses per day and 3 gel capsules (with 0.35 grams of granule per gel capsule) per dose. The dosage of the herbal extract composition, the gel capsule, the nutritional composition, or the pharmaceutical composition of the present invention can be adjusted according to actual situation based on knowledge in the art. The efficacy of the herbal extract composition, the gel capsule, the nutritional composition, or the pharmaceutical composition can be measured by methods known in the art for assessing blood sugar levels in standard animal models (e.g. mice and rats) or in human subjects, for example, as illustrated in Example 11.

EXAMPLES

The following exemplary embodiments further describe the present invention. Although the description refers to practical embodiments, it will be clear to one skilled in the art that the present invention may be practiced with variation of these specific details. Hence this invention should not be construed as limited to the embodiments set forth herein.

Example 1

Preparation of an Herbal Extract Composition

Figure 2:
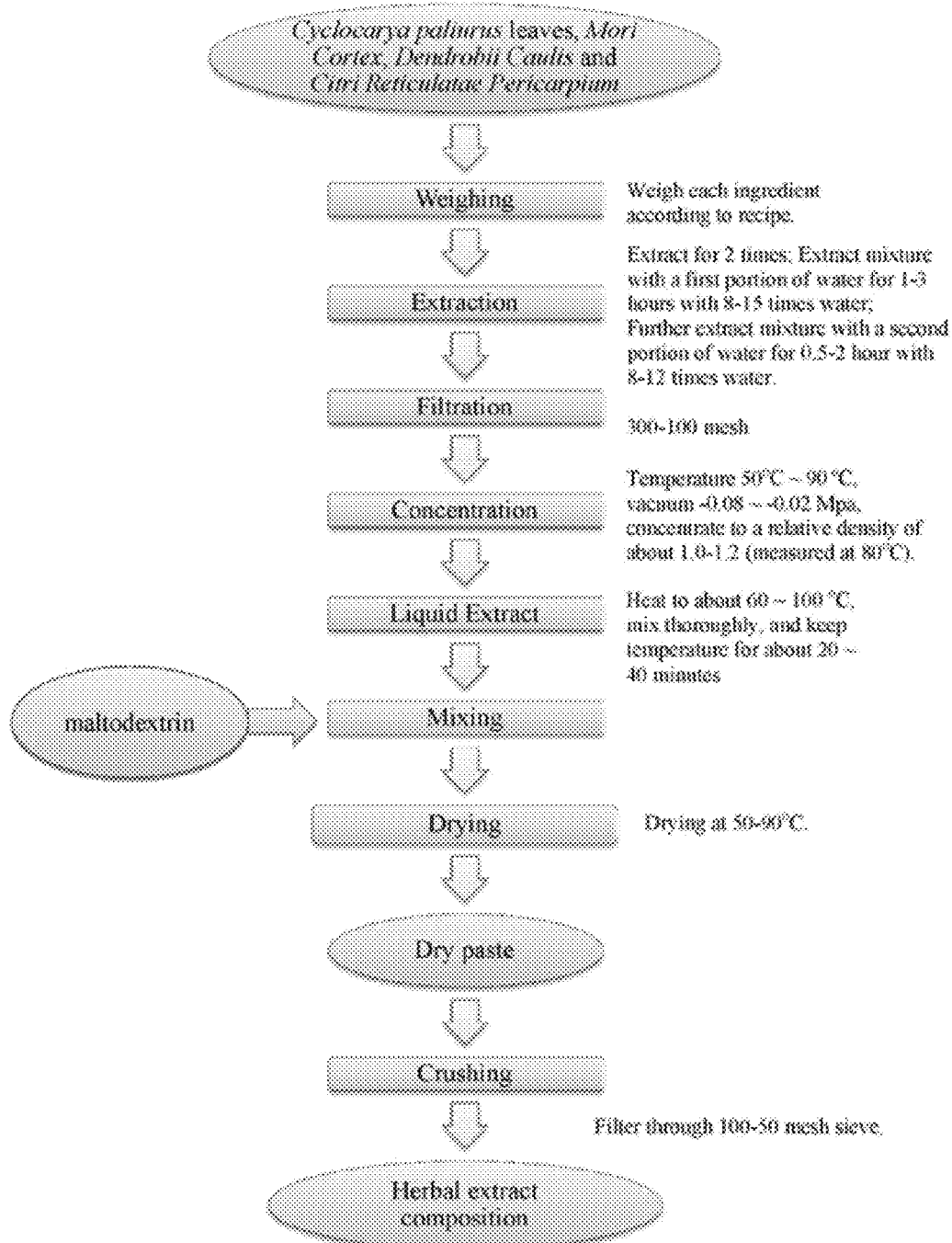

A flow chart illustrating an exemplary method for preparing an herbal extract composition comprising (including consisting essentially of or consisting of) an extract of *Cyclocarya paliurus* leaves, *Mori Cortex, Dendrobii Caulis* and *Citri Reticulatae Pericarpium* is shown in FIG. 1, and described below. A variation of the method is shown in FIG. 2.

The following steps were performed to prepare the herbal extract composition. About grams of *Cyclocarya paliurus* leaves, about 525 grams of *Mori Cortex*, about 300 grams of *Dendrobii Caulis*, and about 150 grams of *Citri Reticulatae Pericarpium* were weighed out according to the recipe shown in Table 2. The weighed *Cyclocarya paliurus* leaves, *Mori Cortex, Dendrobii Caulis* and *Citri Reticulatae Pericarpium* (starting material mixture) were placed into a multi-function extractor. The mixture was extracted two times with water. About 12 times water by weight of the starting material mixture was added for the first extraction, and the mixture was boiled for about 2 hours to obtain a first aqueous extract. About 10 times water by weight of the starting material mixture was then added, and the mixture was boiled for about 1 hour to obtain a second aqueous extract. The first and the second aqueous extracts were combined, and the remnants were discarded. The combined extract was filtered through a 200-mesh filter to obtain a filtrate. The filtrate was concentrated in a vacuum concentrator, in which the temperature was maintained at about 65-80° C., and the vacuum pressure was maintained at about −0.06~−0.04 Mpa, until the concentrated liquid achieved a relative density of about 1.05 (measured at about 60° C.) to obtain a concentrated liquid. The concentrated liquid was placed in cold storage, and allowed to stand for more than about 12 hours at about 4° C. A portion of the supernatant from the concentrated liquid was taken after standing, and the precipitate was discarded. About 60 grams of the excipient (e.g., β-cyclodextrin, maltodextrin, or lactose) (according to recipe in Table 2) was added to the supernatant. The mixture was then kept at 80° C. and mixed thoroughly to obtain a homogenous extract paste. The chamber of a spray dryer was preheated until achieving an in-flow temperature of about 180° C.~200° C. and an out-flow temperature of about 80° C.~100° C. Then, the extract paste was placed in the spray dryer. The flow rate and air speed were adjusted after the extract paste was inside the spray dryer, so that the out-flow temperature was maintained at about 80° C.~100° C. An herbal extract composition was obtained after drying. The herbal extract composition was sealed in a double-layered sterile plastic bag. The method parameters described herein can be adjusted according to actual situation.

Example 2

Preparation of Gel Capsules

Figure 3:
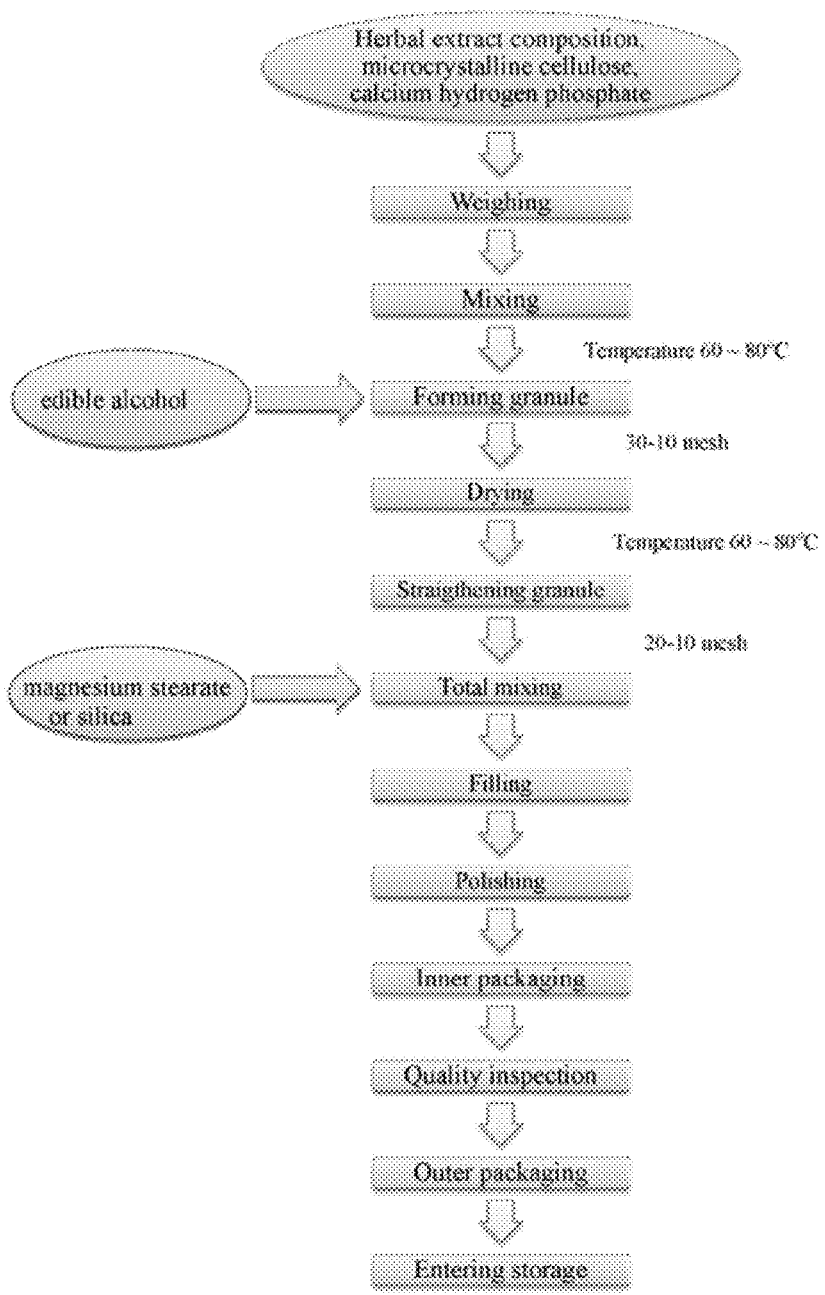
FIG. 3 and FIG. 4 show schematic flow charts of exemplary embodiments of a method for preparing a gel capsule comprising an herbal extract composition comprising (including consisting essentially of or consisting of) an extract of *Cyclocarya paliurus* leaves, *Mori Cortex, Dendrobii Caulis* and *Citri Reticulatae Pericarpium*, which further comprises a microcrystalline cellulose, calcium hydrogen phosphate and magnesium stearate.
Figure 4:
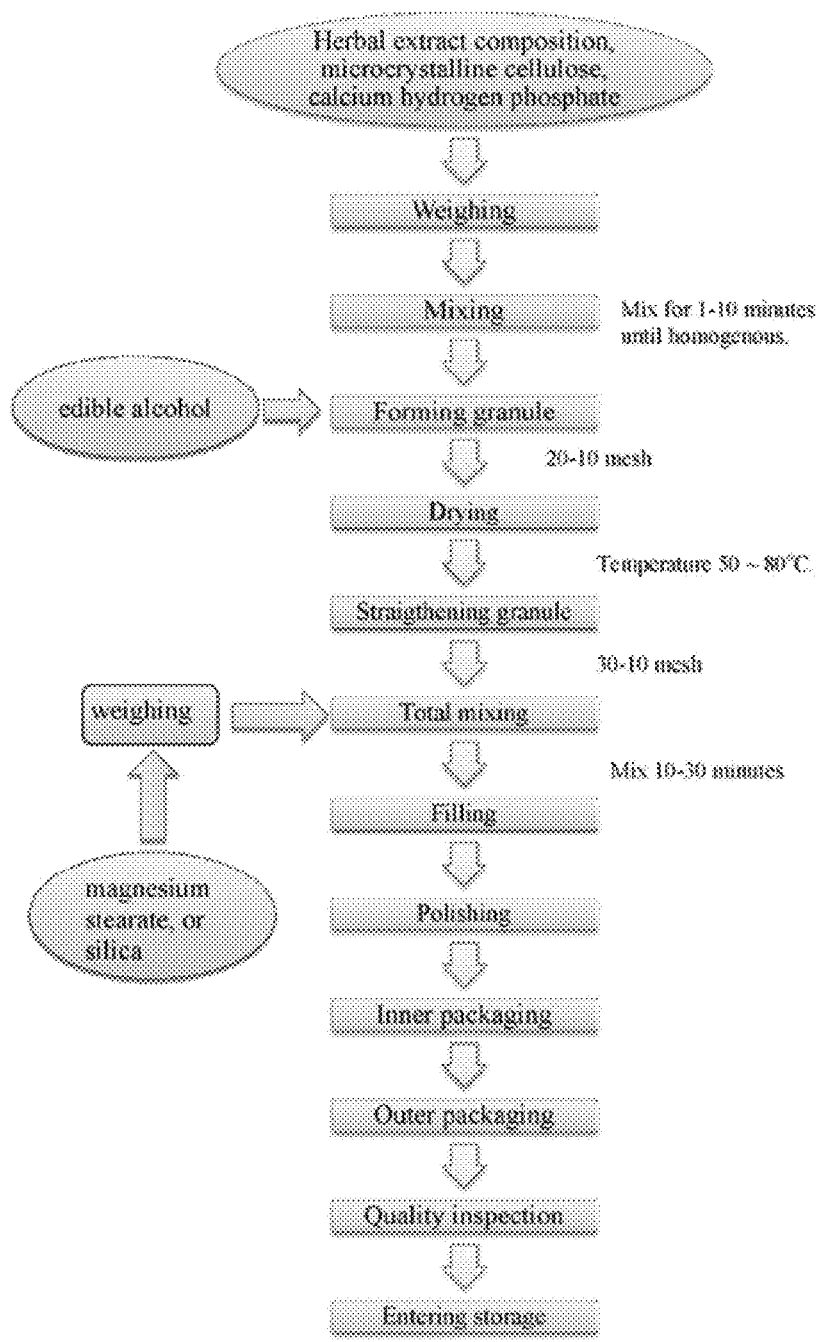

A flow chart illustrating an exemplary method for preparing gel capsules comprising an herbal extract composition comprising (including consisting essentially of or consisting of) an extract of *Cyclocarya paliurus* leaves, *Mori Cortex*, *Dendrobii Caulis* and *Citri Reticulatae Pericarpium* is shown in FIG. 3, and described below. A variation of the method is shown in FIG. 4.

The following steps were performed to prepare the gel capsule. About 30.25 grams of microcrystalline cellulose and about 21 grams of calcium hydrogen phosphate were weighed out according to the recipe in Table 2. An herbal extract composition as prepared by the method in Example 1 was provided. The herbal extract composition, microcrystalline cellulose and calcium hydrogen phosphate were mixed for about 20 minutes to obtain a first uniform mixture. The first mixture was treated with 95% ethanol in food production to obtain a wet granule. The wet granule was sieved through a 20-mesh sieve to remove particles larger than 20-mesh. The sieved wet granule was dried in a drying oven at a temperature of about 65° C.~70° C. to obtain a dry granule containing less than about 5% water. The dry granule was sieved through a 20-mesh sieve to remove particles larger than 20-mesh and to straighten the granule. About 1.75 grams of magnesium stearate was added to the straightened dry granule, and the mixture was mixed thoroughly for about 10 minutes to obtain a uniform granule. A portion of about 0.35 gram of the uniform granule was filled in a size 0 (#0) or size 1 (#1) gel capsule. About 1000 such gel capsules were filled with the total uniform granule. The variation in the weight of granules filled per gel capsule was controlled within ±5%. The gel capsules were polished, and then placed into inner packages according to company standards. The quality of the inner-packaged gel capsules was inspected according to company standards. Then, the inner-packaged gel capsules were placed into outer packages according to company standards. The quality of the packaging was inspected. The packaged gel capsules that have passed quality inspections were entered into storage, and stored in a cool and dry warehouse. The method parameters described herein can be adjusted according to actual situation. For preparation of 1000 gel capsules, 0.35 g/capsule, the yield of the herbal extract composition was about 15.8%.

TABLE 2

Recipe for preparing gel capsules

| Ingredients | Weight |
| --- | --- |
| Main ingredients | |
| *Cyclocarya paliurus* leaves | 525 g |
| Mori Cortex | 525 g |
| Dendrobii Caulis | 300 g |
| Citri Reticulatae Pericarpium | 150 g |
| Auxiliary ingredients | |
| β-cyclodextrin | 60 g |
| microcrystalline cellulose | 30.25 g |
| calcium hydrogen phosphate | 21 g |
| magnesium stearate | 1.75 g |

The weight of auxiliary ingredients can be adjusted according to actual production situation.

Example 3

Removing Heavy Metals by Filtration and Centrifugation

Example 3A

Figure 5:
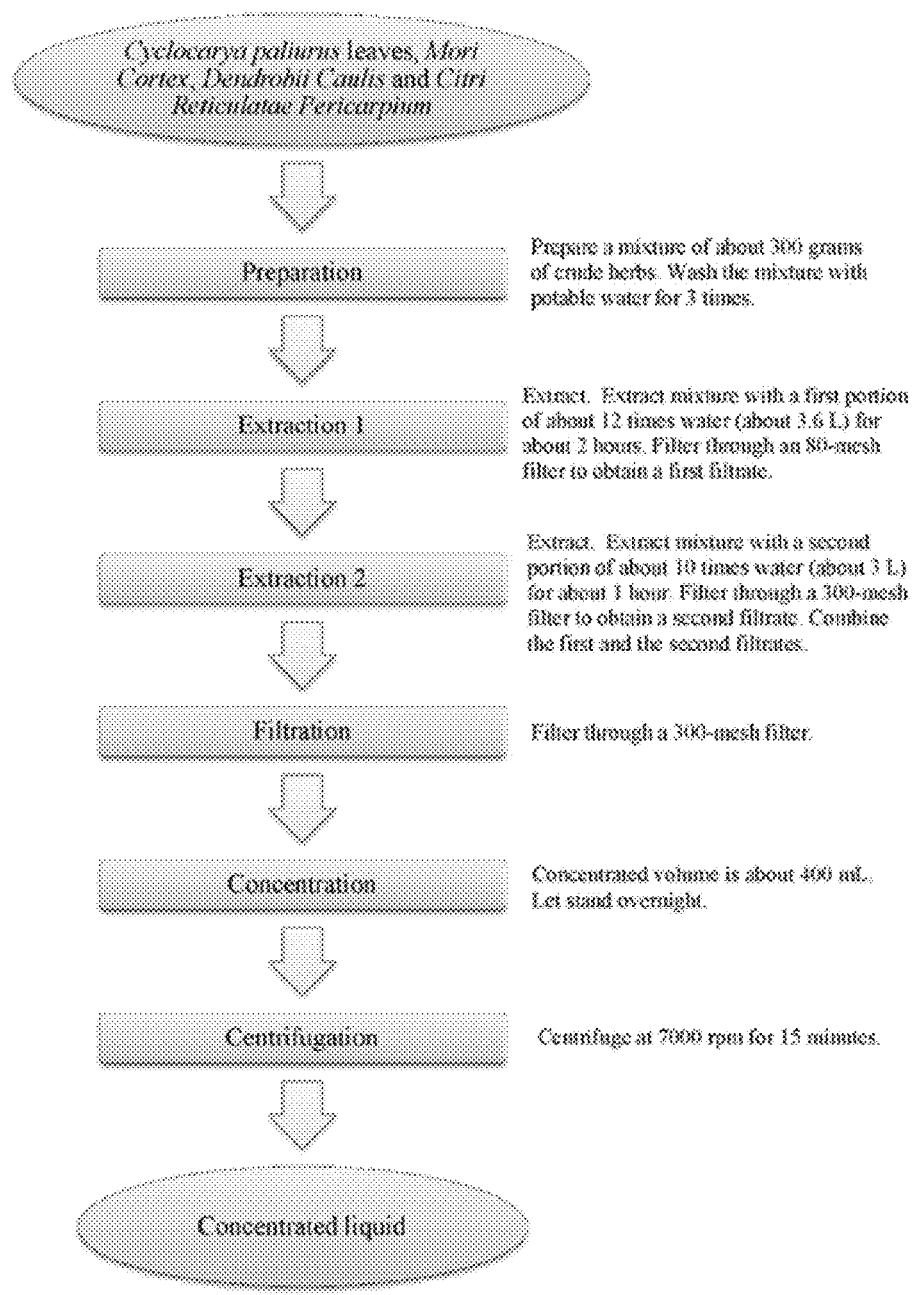
FIG. 5-FIG. 10 show schematic flow charts of exemplary methods for preparing a concentrated liquid from a mixture of *Cyclocarya paliurus* leaves, *Mori Cortex, Dendrobii Caulis* and *Citri Reticulatae Pericarpium* with reduced heavy metal content.

A flow chart illustrating a method for preparing a concentrated liquid with reduced heavy metal contents from a mixture of crude *Cyclocarya paliurus* leaves, *Mori Cortex*, *Dendrobii Caulis* and *Citri Reticulatae Pericarpium* is shown in FIG. 5, and described below.

About 300 grams of a mixture of *Cyclocarya paliurus* leaves, *Mori Cortex*, *Dendrobii Caulis* and *Citri Reticulatae Pericarpium* was prepared, and washed with potable water for 3 times. The mixture was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through a 300-mesh filter to obtain a second filtrate. The first and the second filtrates were combined, and the combined filtrate was filtered through a 300-mesh filter to obtain a third filtrate. The third filtrate was concentrated until the volume was about 400 mL. The concentrated filtrate was centrifuged at 7000 rpm for 15 minutes to give a concentrated liquid that could be further methoded to prepare the herbal extract composition, the herbal extract capsule, the nutritional composition, or the pharmaceutical composition described herein.

Example 3B

Figure 6:
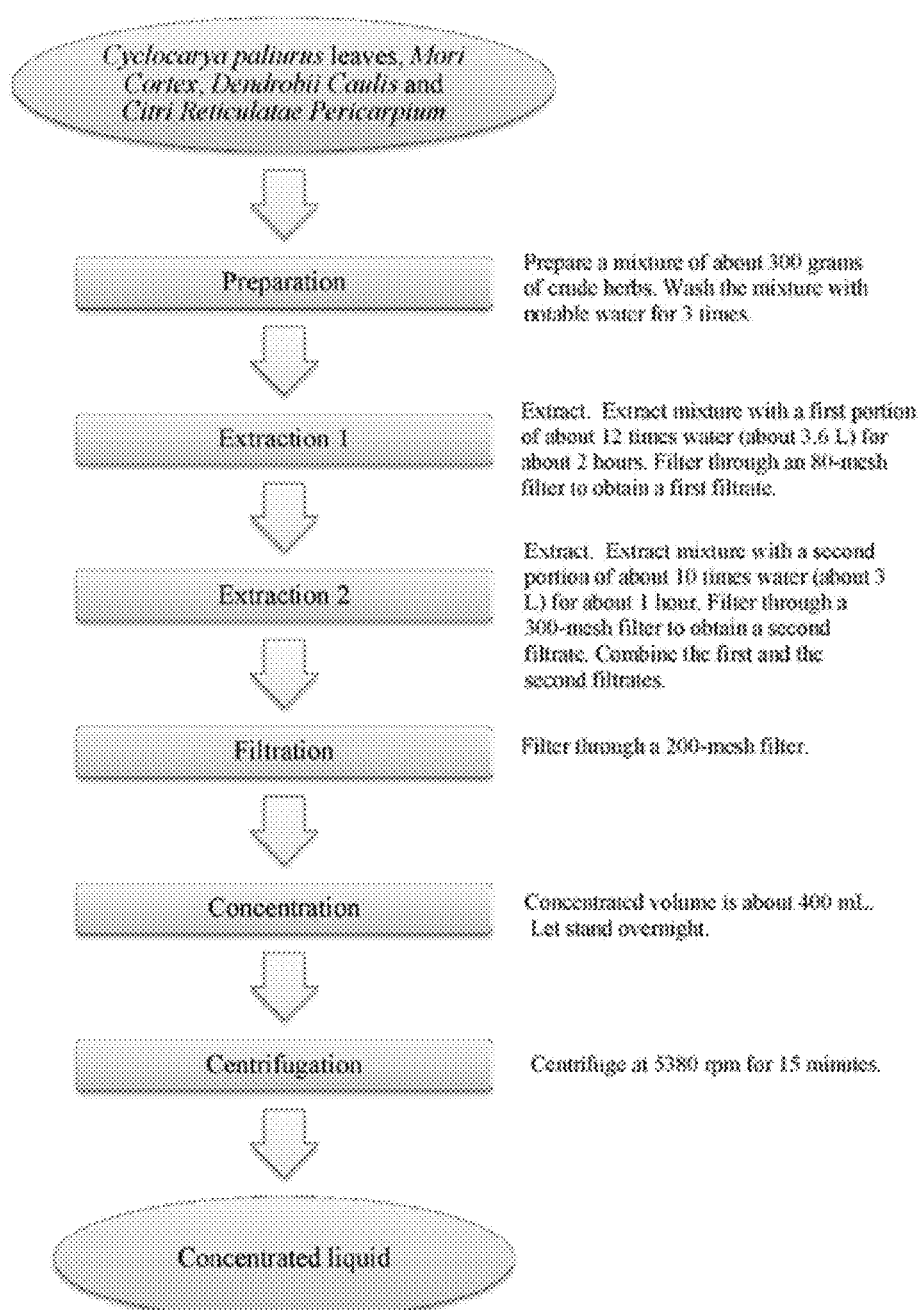

A flow chart illustrating a method for preparing a concentrated liquid with reduced heavy metal contents from a mixture of crude *Cyclocarya paliurus* leaves, *Mori Cortex*, *Dendrobii Caulis* and *Citri Reticulatae Pericarpium* is shown in FIG. 6, and described below.

About 300 grams of a mixture of *Cyclocarya paliurus* leaves (produced in Huang Ao Xiang), *Mori Cortex, Dendrobii Caulis* and *Citri Reticulatae Pericarpium* was prepared, and washed with potable water for 3 times. The mixture was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through an 80-mesh filter to obtain a second filtrate. The first and the second filtrates were combined, and the combined filtrate was filtered through a 200-mesh filter to obtain a third filtrate. The third filtrate was concentrated until the volume was about 400 mL. The concentrated filtrate was centrifuged at 5380 rpm for 15 minutes to give a concentrated liquid that could be further methoded to prepare the herbal extract composition, the herbal extract capsule, the nutritional composition, or the pharmaceutical composition described herein. The concentrations of heavy metals (such as lead and arsenic) and bioactive substances from the herbal extract (such as polysaccharides and flavonoids) in the resulting herbal extract composition consisting essentially of or consisting of an extract from *Cyclocarya paliurus* leaves, *Mori Cortex, Dendrobii Caulis* and *Citri Reticulatae Pericarpium* were measured with methods known in the art. As shown in row 2 of Table 3, for each sample of about 22.613 grams of the herbal extract composition, the concentration of lead was about 0.37 ppm, the concentration of arsenic was about 0.44 ppm, the concentration of polysaccharides was about 11.2% by weight, and the concentration of flavonoids was about 3.69% by weight.

Example 4

Removing Heavy Metals by Filtration

Figure 7:
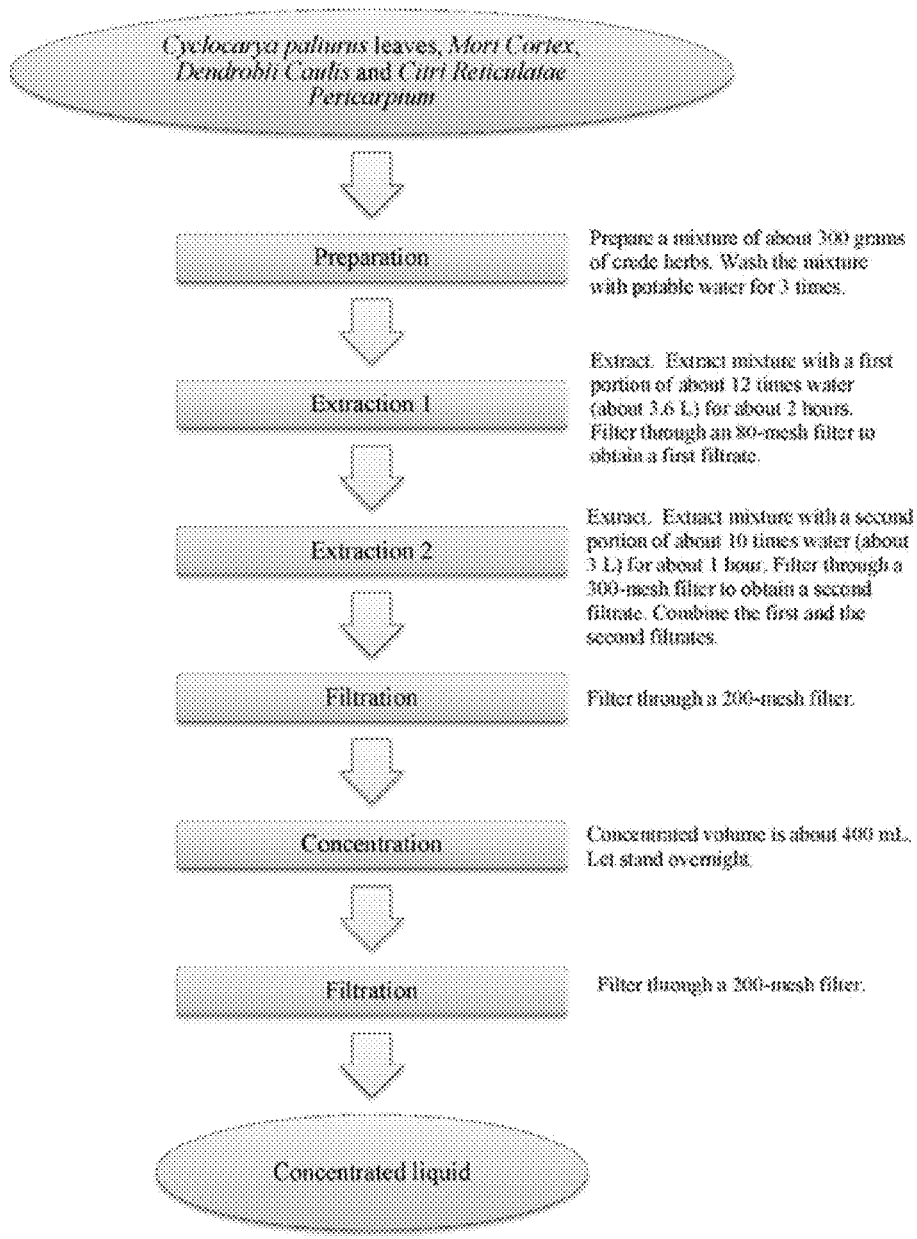

A flow chart illustrating a method for preparing a concentrated liquid with reduced heavy metal contents from a mixture of crude *Cyclocarya paliurus* leaves, *Mori Cortex, Dendrobii Caulis* and *Citri Reticulatae Pericarpium* is shown in FIG. 7, and described below.

About 300 grams of a mixture of *Cyclocarya paliurus* leaves (produced in Huang Ao Xiang), *Mori Cortex, Dendrobii Caulis* and *Citri Reticulatae Pericarpium* was prepared, and washed with potable water for 3 times. The mixture was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through an 80-mesh filter to obtain a second filtrate. The first and the second filtrates were combined, and the combined filtrate was filtered through a 200-mesh filter to obtain a third filtrate. The third filtrate was concentrated until the volume was about 400 mL. The concentrated filtrate was filtered again through a 200-mesh filter to give a concentrated liquid that could be further methoded to prepare the herbal extract composition, the herbal extract capsule, the nutritional composition, or the pharmaceutical composition described herein. The concentrations of heavy metals (such as lead and arsenic) and bioactive substances from the herbal extract (such as polysaccharides and flavonoids) in the resulting herbal extract composition consisting essentially of or consisting of an extract from *Cyclocarya paliurus* leaves, *Mori Cortex, Dendrobii Caulis* and *Citri Reticulatae Pericarpium* were measured with methods known in the art. As shown in row 1 of Table 3, for each sample of about 22.733 grams of the herbal extract composition, the concentration of lead was about 0.64 ppm, the concentration of arsenic was about 0.44 ppm, the concentration of polysaccharides was about 12.2% by weight, and the concentration of flavonoids was about 3.88% by weight.

Example 5

Removing Heavy Metals by Filtration and Addition of Chitosan

Example 5A

Figure 8:
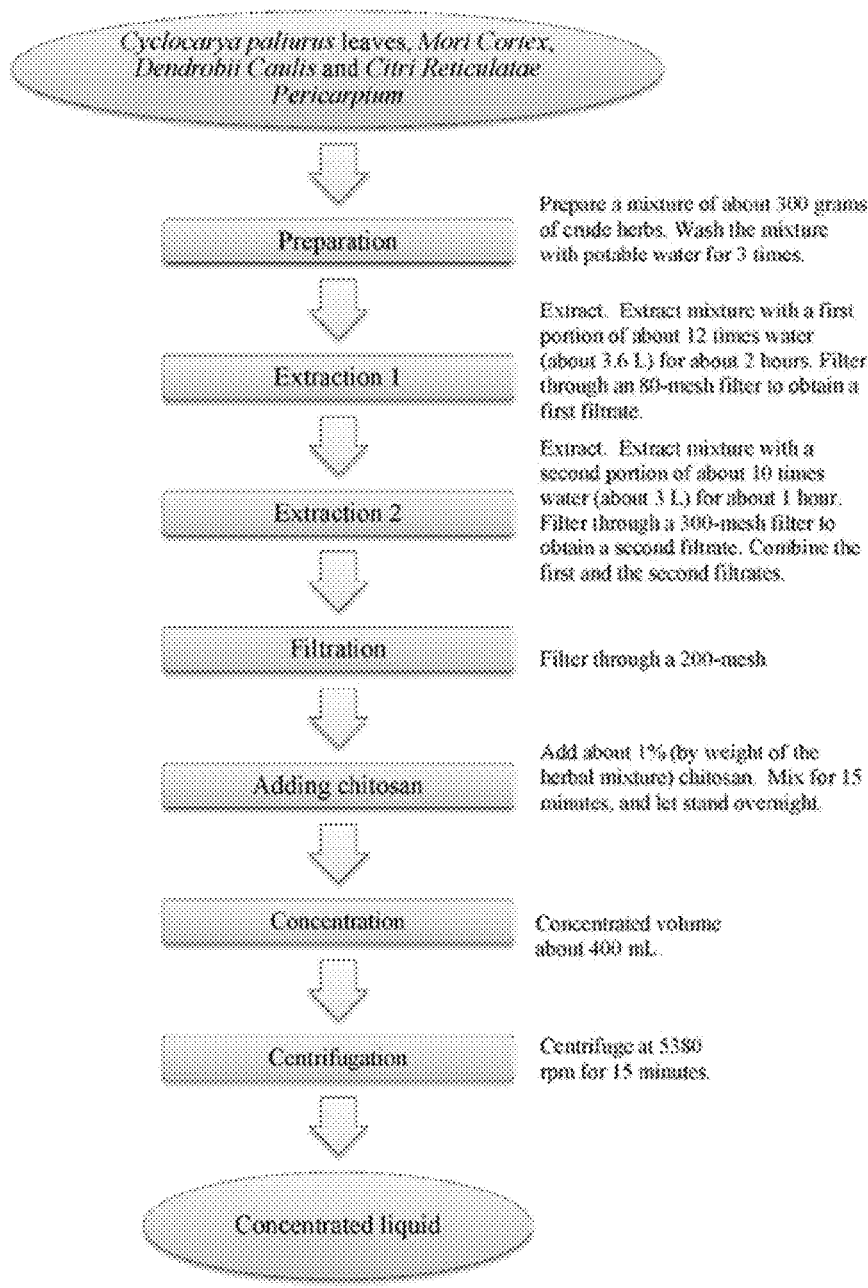

A flow chart illustrating a method for preparing a concentrated liquid with reduced heavy metal contents from a mixture of crude *Cyclocarya paliurus* leaves, *Mori Cortex, Dendrobii Caulis* and *Citri Reticulatae Pericarpium* is shown in FIG. 8, and described below.

About 300 grams of a mixture of *Cyclocarya paliurus* leaves (lead concentration is about 3.0 ppm), *Mori Cortex, Dendrobii Caulis* and *Citri Reticulatae Pericarpium* was prepared, and washed with potable water for 3 times. The mixture was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through an 80-mesh filter to obtain a second filtrate. The first and the second filtrates were combined, and the combined filtrate was filtered through a 200-mesh filter to obtain a third filtrate. About 1% by weight of the herbal mixture of chitosan was added to the third filtrate. The filtrate with chitosan was mixed for about 15 minutes, and the mixed filtrate with chitosan was allowed to stand over night. The mixed filtrate was then filtered through a 200-mesh filter, and then concentrated to about 400 mL. The concentrated filtrate was then centrifuged at 5380 rpm for 15 minutes to give a concentrated liquid that could be further methoded to prepare the herbal extract composition, the herbal extract capsule, the nutritional composition, or the pharmaceutical composition described herein. The concentrations of heavy metals (such as lead and arsenic) and bioactive substances from the herbal extract (such as polysaccharides and flavonoids) in the resulting herbal extract composition consisting essentially of or consisting of an extract from *Cyclocarya paliurus* leaves, *Mori Cortex, Dendrobii Caulis* and *Citri Reticulatae Pericarpium* were measured with methods known in the art. As shown in row 3 of Table 3, for each sample of about 19.060 grams of the herbal extract composition, the concentration of lead was about 0.52 ppm, the concentration of arsenic was about 0.59 ppm, the concentration of polysaccharides was about 10.1% by weight, and the concentration of flavonoids was about 3.04% by weight.

Example 5B

Figure 9:
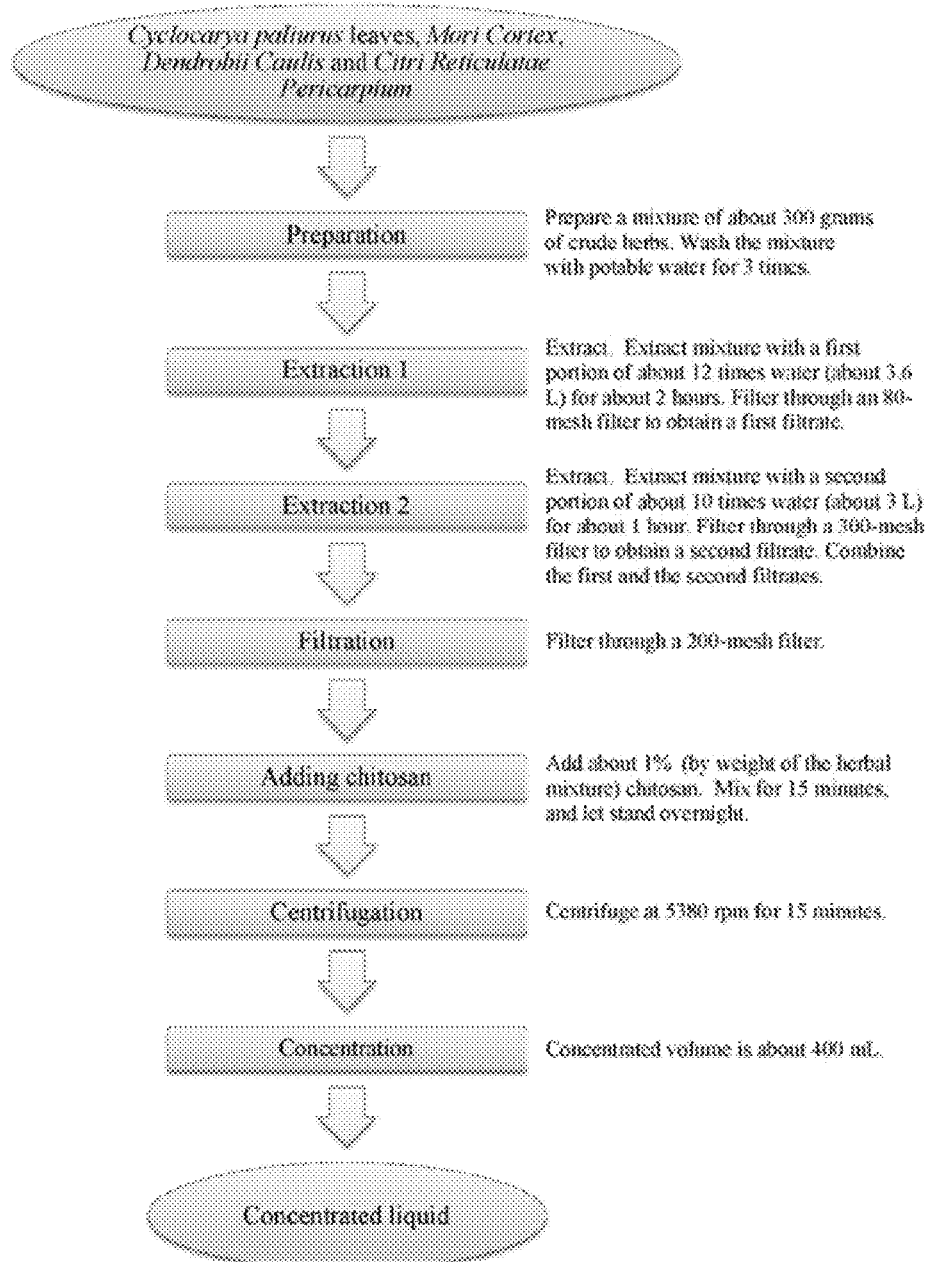

A flow chart illustrating a method for preparing a concentrated liquid with reduced heavy metal contents from a mixture of crude *Cyclocarya paliurus* leaves, *Mori Cortex, Dendrobii Caulis* and *Citri Reticulatae Pericarpium* is shown in FIG. 9, and described below.

About 300 grams of a mixture of *Cyclocarya paliurus* leaves (lead concentration is about 3.0 ppm), *Mori Cortex, Dendrobii Caulis* and *Citri Reticulatae Pericarpium* was prepared, and washed with potable water for 3 times. The mixture was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through an 80-mesh filter to obtain a second filtrate. The first and the second filtrates were combined, and the combined filtrate was filtered through a 200-mesh filter to obtain a third filtrate. About 1% (by weight of the herbal mixture) of chitosan was added to the third filtrate. The filtrate with chitosan was mixed for about 15 minutes, and the mixed filtrate with chitosan was allowed to stand over night. The mixed filtrate was then centrifuged at 5380 rpm for 15 minutes, and concentrated to about 400 mL to give a concentrated liquid that could be further methoded to prepare the herbal extract composition, the herbal extract capsule, the nutritional composition, or the pharmaceutical composition described herein.

Example 6

Removing Heavy Metals by Filtration and Addition of Potassium Carbonate

Figure 10:
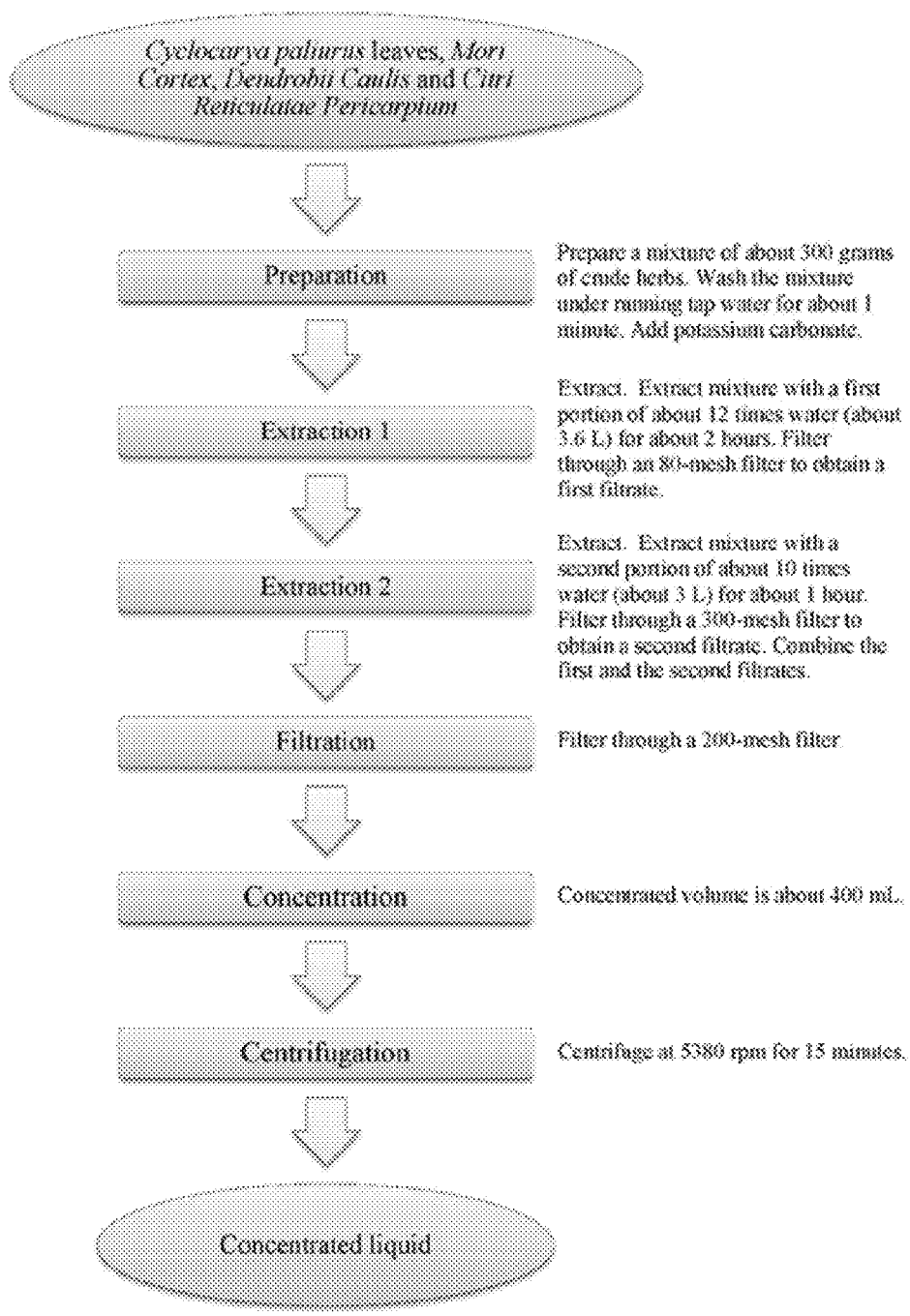

A flow chart illustrating a method for preparing a concentrated liquid with reduced heavy metal contents from a mixture of crude *Cyclocarya paliurus* leaves, *Mori Cortex, Dendrobii Caulis* and *Citri Reticulatae Pericarpium* is shown in FIG. 10, and described below.

About 300 grams of a mixture of *Cyclocarya paliurus* leaves (produced by Huang Ao Xiang), *Mori Cortex, Dendrobii Caulis* and *Citri Reticulatae Pericarpium* was prepared, and washed under running tap water for about 1 minute. Potassium carbonate was added to the washed mixture. The mixture with potassium carbonate was extracted two times with water by boiling. About 12 times water by weight of the crude herbal mixture (about 3.6 L) was added for the first extraction, and the mixture was boiled for about 2 hours to obtain a first aqueous extract. The first aqueous extract was filtered through an 80-mesh filter to obtain a first filtrate. About 10 times water by weight of the crude herbal mixture (about 3 L) was then added, and the mixture was boiled for about 1 hour to obtain a second aqueous extract. The second aqueous extract was filtered through an 80-mesh filter to obtain a second filtrate. The first and the second filtrates were combined, and the combined filtrate was filtered through a 200-mesh filter, and then concentrated to about 400 mL. The concentrated filtrate was then centrifuged at 5380 rpm for 15 minutes to give a concentrated liquid that could be further methoded to prepare the herbal extract composition, the herbal extract capsule, the nutritional composition, or the pharmaceutical composition described herein. The concentrations of heavy metals (such as lead and arsenic) and bioactive substances from the herbal extract (such as polysaccharides and flavonoids) in the resulting herbal extract composition consisting essentially of or consisting of an extract from *Cyclocarya paliurus* leaves, *Mori Cortex, Dendrobii Caulis* and *Citri Reticulatae Pericarpium* were measured with methods known in the art. As shown in row 4 of Table 3, for each sample of about 15.225 grams of the herbal extract composition, the concentration of lead was about 0.71 ppm, the concentration of arsenic was about 0.54 ppm, the concentration of polysaccharides was about 13.0% by weight, and the concentration of flavonoids was about 3.41% by weight.

TABLE 3

Heavy metals, polysaccharides, and flavonoids in herbal extract compositions

| Method | Solid materials (g) | Lead (ppm) | Arsenic (ppm) | Polysaccharides (%) | Flavonoids (%) |
| --- | --- | --- | --- | --- | --- |
| Filtration[1] | 22.733 | 0.64 | 0.44 | 12.2 | 3.88 |
| Filtration and centrifugation[1] | 22.613 | 0.37 | 0.44 | 11.2 | 3.69 |
| Filtration and addition of chitonsan[2] | 19.06 | 0.52 | 0.59 | 10.1 | 3.04 |
| Filtration and addition of potassium carbonate[1] | 15.225 | 0.71 | 0.54 | 13 | 3.41 |

[1]*Cyclocarya paliurus* leaves from Huang Ao Xiang (See Table 1)
[2]*Cyclocarya paliurus* leaves with lead concentration of about 3.0 ppm.

Example 7

Preparation of Test Samples and Control Samples

Sample Formulae:

Test Sample 1 (S1): *Cyclocarya paliurus* leaves: 1.0 kg; *Mori Cortex:* 8.0 kg; *Dendrobii Caulis:* 0.5 kg; and *Citri Reticulatae Pericarpium:* 0.5 kg.

Test Sample 2 (S2): *Cyclocarya paliurus* leaves: 2.0 kg; *Mori Cortex:* 0.5 kg; *Dendrobii Caulis:* 7.0 kg; and *Citri Reticulatae Pericarpium:* 0.5 kg.

Test Sample 3 (S3): *Cyclocarya paliurus* leaves: 3.5 kg; *Mori Cortex:* 3.5 kg; *Dendrobii Caulis:* 2.0 kg; and *Citri Reticulatae Pericarpium:* 1.0 kg.

Test Sample 4 (S4): *Cyclocarya paliurus* leaves: 6.0 kg; *Mori Cortex*: 2.0 kg; *Dendrobii Caulis*: 1.0 kg; *Polygonati odorati Rhizoma*: 0.5 kg; and *Poria*: 0.5 kg.

Test Sample 5 (S5): *Cyclocarya paliurus* leaves: 8.0 kg; *Mori Cortex*: 0.5 kg; *Dendrobii Caulis*: 0.5 kg; *Angelicae sinensis Radix*: 0.5 kg, and *Rhodiolae Crenulatae Radix et Rhizoma*: 0.5 kg.

Test Sample 6 (S6): *Cyclocarya paliurus* leaves: 1.0 kg; *Corni Fructus*: 1.0 kg; *Anemarrhenae Rhizoma*: 1.0 kg; *Ginseng Radix* et *Rhizoma*: 1.0 kg; *Lycii Fructus*: 1.0 kg; *Ligustri lucidi Fructus*: 1.0 kg; *Ophiopogonis Radix*: 1.0 kg; Prepared Rhubarb: 1.0 kg; *Schisandrae chinensis Fructus*: 1.0 kg; and *Tribuli Fructus*: 1.0 kg.

Control Sample 1 (D1): *Cyclocarya paliurus* leaves: 10 kg.

Control Sample 2 (D2): *Mori Cortex*: 10 kg.

Control Sample 3 (D3): *Dendrobii Caulis*: 10 kg.

The samples were prepared according to the steps detailed below, and tested for efficacies in lowering blood sugars, blood lipids, and blood pressure in animal models.

Method of Preparation

Step 1. Each herbal medicine was weighed precisely according to the formula above, washed with clean water; extracted twice by boiling with 12 times (by weight) of water for 2 hours, and with 10 times (by weight) of water for 1 hour; and 100-mesh filtered.

Step 2. The extracts were combined and filtered; the filtrate was concentrated to a relative density of 1.05-1.08 when measured at 60° C.; and saved for later use.

Step 3. β-cyclodextrin was added to the filtrate according to formula ratio. The mixture was heated to 85° C., mixed well by stirring, and let stand for 30 mins under constant temperature.

Step 4. The filtrate was placed in a spray drier. The chamber was pre-heated, and the filtrate was allowed to enter when the inlet air temperature reached 210° C.±10° C. The flow rate and air speed were adjusted, and the outlet air temperature was controlled at 95° C.+5° C. to obtain an extract powder, which was sealed in a double-layered clean plastic bag.

Step 5. Microcrystalline cellulose, calcium hydrogen phosphate, silicon dioxide, and Magnesium stearate were weighed according to formula ratio, mixed well for 3-5 mins to obtain a mixture.

Step 6. The mixture was made into a soft material using 80% edible alcohol, and wet granules were obtained after passing a 14-mesh sieve. The wet granules were dried until containing ≤5.0% water. The dried granules were passed through 16-mesh sieve for straightening, to obtain dry granules.

Step 7. The whole mixture was filled into #1 capsules, 0.3 g per capsule.

Example 8

Test of Lowering Blood Sugar

1. Materials and Methods

1) Samples and solution: samples from Test Samples 1-6 and Control Samples 1-3 were labeled as S1, S2, S3, S4, S5, S6, and D1, D2, D3, respectively; Streptozotocin (SIGMA), pack size: 1 g/tube, lot#: SLBJ7785V; insulin detection kit, imported and aliquoted, Nanjing Jiancheng Bioengineering Co., 20141022; 0.9% NaCl injection (physiological saline), pack size: 250 mL/bottle, Sichuan Kelun Pharmaceutical Co. Ltd., lot#: C13102005-1; high fat diet formula (79% basal diet+1% cholesterol+15% fresh yolk+5% lard), picric acid, etc.

2) Instruments: W-80A vortex mixer (Shanghai Medical Instruments Co. Ltd.); electronic balance, METTLER TOLEDO (METTLER-TOLEDO group), model: pl303; LDZ5-2 centrifuge (Beijing Medical Centrifuge Factory); Johnson Stable Blood Glucose Meter (Johnson & Johnson (China) Medical Device Co. Ltd.); BECKMAN Synchron CX 5 automatic blood biochemistry analyzer (USA); microplate reader, Bio-Rad (USA), model: iMark; DCA 2000 glycosylated hemoglobin analyzer (Bayer, Germany); others: platform scale, and fixed cage, etc.

3) Experimental animals: SD rats (SPF level), weight 160-180 g, male, provided by Southern Medical University Laboratory Animal Center, Certificate#: SCXK(Guangdong) 2011-0015. Animals were raised in SPF level barrier level animal room, animal use license#: SYXK(Guangdong) 2012-0081.

4) Dosage setting: expected dosage for human adults is 3.0 g/60 kg·BW·day. Dosage used for rats was 10 times that of human. The dosage was calculated using raw drug amount.

5) Statistical analysis: data were processed using SPSS 17.0 statistical tool, parameters were displayed as mean standard deviation ($\bar{x}\pm S$), ANOVA test was used for comparison among groups, $p<0.05$ was defined as statistically significant.

2. Methods and Results 2.1 Methods

1) Rat diet: Regular diet: cornmeal 80%, flour 15%, soybean flour 5%; High fat diet: 79% basal diet+1% cholesterol+15% fresh yolk+5% lard.

2) Modeling: 110 SPF level SD rats, male, weight 160-180 g, were fed for one week adaptively. 10 rats were selected as normal control group and fed with regular diet, while animals of other groups were fed with high fat diet for one month, after random inspection showing an obvious elevation in blood lipid indexes, STZ was intraperitoneally injected at 35 mg/kg to induce diabetic models (before injecting, STZ was prepared into 6 mg/mL solution using 0.1 mmol/L citric acid/sodium citrate buffer (pH=4.5), and destined to be finished within 60 mins). Fasting venous blood was collected from tails on the $7^{th}$ day after STZ injection. Blood sugar was measured using blood sugar meter, and successful models were regarded as with blood sugar ≥16.7 mmol/L. After the models were stable, animals were grouped based on blood lipids and blood sugar, orally administered test drugs and control drugs, and all indexes were monitored.

3) Grouping and drug administration: 100 successfully modeled animals in relatively good conditions were evenly separated into 10 groups based on blood sugar levels and weights: 10 rats per group, named as type II diabetes model control group (administered with distilled water), S1 group, S2 group, S3 group, S4 group, S5 group, S6 group, D1 group, D2 group, and D3 group. Normal un-modeled SD rats were set as normal control (administered with distilled water). Each group was orally administered with drug according to corresponding dosage, once per day, for a period of 4 weeks (4 W).

2.2 Measurements

1) Regular observation was performed, and weights were recorded every 2 weeks.

2) Blood sugar was measured before and after 4 weeks of drug administration, using blood sugar meter.

3) Sugar tolerance test: the test was carried out 2 days before the whole experiment ended. Sugar tolerance test was carried out as following: animals were kept under fasting for about 6 hours, different concentrations of test samples were given to each group, glucose was orally administered at 2.0 g/kg after 15-20 mins, blood sugar levels were measured at 0, 0.5, and 2 hours after administering glucose, and the changes of areas under the blood sugar curve of each time point after administering glucose were studied for both control groups and experimental groups. The area under the blood sugar curve=½×(blood sugar level at 0 h+blood sugar level at 0.5 h)×0.5+½×(blood sugar level at 2 h+blood sugar level at 0.5 h)×1.5=0.25×(blood sugar level at 0 h+4×blood sugar level at 0.5 h+3×blood sugar level at 2 h).

2.3 Results

1) The effect on blood sugar level of type II diabetes rats: As shown in Table 4, the rat blood sugar level of each diabetes model group significantly elevated before drugs are given, compared to that of the normal control group, indicating successful modeling. After 4 W of treatment, the blood sugar levels of S1-S6 groups and D1 group all decreased.

TABLE 4

The effect of samples on blood sugar level of type II diabetes rats ($\bar{x} \pm S$)

| Group | n | Blood sugar before treatment (mmol/L) | Blood sugar after 4 W treatment (mmol/L) |
|---|---|---|---|
| Normal control group | 10 | 5.37 ± 1.10 | 5.41 ± 1.05 |
| Model control group | 10 | 19.91 ± 4.23[##] | 21.90 ± 4.16[##] |
| S1 group | 10 | 19.83 ± 4.85 | 16.18 ± 3.63* |
| S2 group | 10 | 19.95 ± 4.17 | 16.29 ± 4.02* |
| S3 group | 10 | 19.12 ± 4.08 | 15.48 ± 3.81** |
| S4 group | 10 | 18.99 ± 3.90 | 16.04 ± 3.28* |
| S5 group | 10 | 19.92 ± 3.81 | 16.08 ± 3.52* |
| S6 group | 10 | 19.93 ± 3.89 | 16.31 ± 3.26* |
| D1 group | 10 | 18.97 ± 4.06 | 16.65 ± 3.80* |
| D2 group | 10 | 18.95 ± 3.57 | 18.90 ± 4.65 |
| D3 group | 10 | 19.34 ± 4.55 | 18.53 ± 3.89 |

Note:
compared to normal control group: [##]$p < 0.01$;
compared to model control group: *$p < 0.05$, **$p < 0.01$.

2) The sugar tolerance test results of type II diabetes rats: As shown in Table 5, the areas under the blood sugar curves of S1-S6 groups and D1 group all decreased, compared to that of model control group.

TABLE 5

The effect of samples on sugar tolerance of type II diabetes rats ($\bar{x} \pm S$)

| Group | n | Area under blood sugar curve |
|---|---|---|
| Normal control group | 10 | 16.86 ± 2.06 |
| Model control group | 10 | 37.64 ± 6.38[##] |
| S1 group | 10 | 26.74 ± 6.75* |
| S2 group | 10 | 28.53 ± 5.97* |
| S3 group | 10 | 24.81 ± 5.60** |
| S4 group | 10 | 27.88 ± 6.72* |
| S5 group | 10 | 28.17 ± 7.35* |
| S6 group | 10 | 28.34 ± 5.79* |
| D1 group | 10 | 30.33 ± 5.87* |
| D2 group | 10 | 33.24 ± 6.71 |
| D3 group | 10 | 34.30 ± 6.89 |

Note:
compared to normal control group: [#]$p < 0.05$, [##]$p < 0.01$;
compared to model control group: $p > 0.05$ for all.

3. Conclusion

S1-S6 and D1 showed clear effects on lowering blood sugar for diabetes rat models, and the compositions of S1-S6 exhibited synergistic or enhanced effects in lowering blood sugar.

Example 9

Test of Lowering Blood Lipids

1. Materials and Methods

1) Samples and solution: samples from Test Samples 1-6 and Control Samples 1-3 were labeled as S1, S2, S3, S4, S5, S6, and D1, D2, D3, respectively; 0.9% NaCl injection (physiological saline), pack size: 250 mL/bottle, Sichuan Kelun Pharmaceutical Co. Ltd., lot#: C13102005-1; high fat diet formula (79% basal diet+1% cholesterol+15% fresh yolk+5% lard), distilled water, and picric acid, etc.

2) Instruments: W-80A vortex mixer (Shanghai Medical Instruments Co. Ltd.); electronic balance, METTLER TOLEDO (METTLER-TOLEDO group), model: pl303; LDZ5-2 centrifuge (Beijing Medical Centrifuge Factory); BECKMAN Synchron CX 5 automatic blood biochemistry analyzer (USA); others: platform scale, and fixed cage, etc.

3) Experimental animals: SD rats (SPF level), weight 160-180 g, male, provided by Southern Medical University Laboratory Animal Center, Certificate#: SCXK(Guangdong) 2011-0015. Animals were raised in SPF level barrier level animal room, animal use license#: SYXK(Guangdong) 2012-0081.

4) Dosage setting: expected dosage for human adults is 3.0 g/60 kg·BW·day. Dosage used for rats was 10 times that of human. The dosage was calculated using raw drug amount.

5) Statistical analysis: data were processed using SPSS 17.0 statistical tool, parameters were displayed as mean±standard deviation ($\bar{x} \pm S$), ANOVA test was used for comparison among groups, $p < 0.05$ was defined as statistically significant.

2. Methods and Results 2.1 Grouping and Methods

SPF level SD rats, male, weight 160-180 g, were fed for one week adaptively. 10 rats were selected as normal control group and fed with regular diet; the rest animals were fed with high fat diet. After feeding continuously for 4 weeks (blood was drawn at regular intervals to test for the four indexes of blood lipids, in order to determine whether models were successful), 100 successfully modeled animals in relatively good conditions were chosen and evenly separated into 10 groups based on blood lipid levels and weights: 10 rats per group, named as hyperlipidemia model control group (administered with distilled water), S1 group, S2 group, S3 group, S4 group, S5 group, S6 group, D1 group, D2 group, and D3 group.

After feeding high fat diet for 4 weeks, drugs were administered according to the above grouping with high fat diet continuously provided (the normal control group was fed with normal diet), drugs were administered once per day, for a period of 4 W. After the last drug administration, animals were kept overnight fasting, weighed the next day, then anaesthetized using chloral hydrate, after drawing blood through inferior vena cava, animals were executed. Supernatant was obtained by centrifuging the blood samples, then serum biochemical indexes were measured.

2.2 Measurements

1) Regular observation was performed, and weights were recorded every week.

2) Rat serum lipid indexes of each group: blood was drawn from orbital venous plexus every 2 weeks, serum was separated for detection of: total cholesterol (TC), triglyceride (TG), high-density lipoprotein cholesterol (HDL-C), and low-density lipoprotein cholesterol (LDL-C).

2.3 Results

The effects on serum TC, TG, HDL-C, LDL-C, and TC/HDL-C are shown in Tables 6 and 7. As shown in Table 6, after fed with high fat diet for 4 W, the model control group rats had significantly elevated levels of TC and LDL-C ($p<0.01$), and clear increase of TG ($p<0.05$), compared to those of normal control group, indicating successful modeling of hyperlipidemia rats. Rats were evenly separated into 4 groups according to blood lipid level. As can be seen from Table 7, after 4 W treatment, drug samples of S1-S6 groups and D1 group could lower TC, TG and LDL-C levels in serum ($p<0.05$ or $p<0.01$), compared to the model control group.

TABLE 6

Serum lipid data of successfully modeled evenly grouped rats ($\bar{x} \pm S$)

| Group | n | TC (mmol/L) | TG (mmol/L) | HDL-C (mmol/L) | LDL-C (mmol/L) |
|---|---|---|---|---|---|
| Normal control group | 10 | 1.30 ± 0.15 | 1.46 ± 0.58 | 0.59 ± 0.06 | 0.29 ± 0.03 |
| Model control group | 10 | 2.11 ± 0.31## | 2.10 ± 0.41## | 0.58 ± 0.07 | 0.45 ± 0.07## |
| S1 group | 10 | 2.13 ± 0.37 | 2.05 ± 0.40 | 0.58 ± 0.05 | 0.44 ± 0.04 |
| S2 group | 10 | 2.17 ± 0.38 | 2.00 ± 0.39 | 0.60 ± 0.10 | 0.45 ± 0.09 |
| S3 group | 10 | 2.09 ± 0.32 | 2.10 ± 0.57 | 0.59 ± 0.08 | 0.45 ± 0.07 |
| S4 group | 10 | 2.07 ± 0.30 | 2.08 ± 0.53 | 0.60 ± 0.08 | 0.46 ± 0.09 |
| S5 group | 10 | 2.04 ± 0.25 | 2.05 ± 0.47 | 0.58 ± 0.10 | 0.43 ± 0.10 |
| S6 group | 10 | 1.99 ± 0.34 | 2.08 ± 0.45 | 0.60 ± 0.08 | 0.45 ± 0.09 |
| D1 group | 10 | 2.01 ± 0.35 | 2.10 ± 0.50 | 0.58 ± 0.11 | 0.44 ± 0.08 |
| D2 group | 10 | 1.99 ± 0.47 | 2.12 ± 0.49 | 0.58 ± 0.08 | 0.46 ± 0.09 |
| D3 group | 10 | 2.05 ± 0.32 | 2.08 ± 0.62 | 0.59 ± 0.06 | 0.47 ± 0.10 |

Note:
compared to normal control group: #$p < 0.05$, ##$p < 0.01$;
compared to model control group: $p > 0.05$ for all.

TABLE 7

Rat serum lipid data of each group after 4 W of drug administration ($\bar{x} \pm S$)

| Group | n | TC (mmol/L) | TG (mmol/L) | HDL-C (mmol/L) | LDL-C (mmol/L) |
|---|---|---|---|---|---|
| Normal control group | 10 | 1.35 ± 0.47 | 1.55 ± 0.53 | 0.60 ± 0.07 | 0.34 ± 0.07 |
| Model control group | 10 | 2.61 ± 0.52## | 2.76 ± 0.50## | 0.59 ± 0.07 | 0.69 ± 0.11## |
| S1 group | 10 | 2.08 ± 0.56* | 2.01 ± 0.52* | 0.58 ± 0.08 | 0.50 ± 0.07* |
| S2 group | 10 | 2.04 ± 0.58* | 2.11 ± 0.47* | 0.56 ± 0.10 | 0.51 ± 0.08* |
| S3 group | 10 | 1.89 ± 0.45** | 2.15 ± 0.46* | 0.58 ± 0.10 | 0.49 ± 0.09* |
| S4 group | 10 | 2.13 ± 0.54* | 2.05 ± 0.39* | 0.60 ± 0.07 | 0.50 ± 0.08* |
| S5 group | 10 | 2.11 ± 0.48* | 2.15 ± 0.41* | 0.58 ± 0.11 | 0.49 ± 0.09* |
| S6 group | 10 | 2.10 ± 0.55* | 2.03 ± 0.42* | 0.57 ± 0.07 | 0.52 ± 0.08* |
| D1 group | 10 | 2.17 ± 0.39* | 2.05 ± 0.45* | 0.59 ± 0.10 | 0.51 ± 0.07* |
| D2 group | 10 | 2.53 ± 0.61 | 2.66 ± 0.51 | 0.58 ± 0.08 | 0.64 ± 0.11 |
| D3 group | 10 | 2.55 ± 0.59 | 2.61 ± 0.43 | 0.60 ± 0.10 | 0.63 ± 0.09 |

Note:
compared to normal control group: #$p < 0.05$, ##$p < 0.01$;
compared to model control group: *$p < 0.05$, **$p < 0.01$.

3. Conclusion

S1-S6 and D1 showed clear effects in lowering blood lipid levels in hyperlipidemia rat models, and the compositions of S1-S6 exhibited synergistic or enhanced effects in lowering blood lipids.

Example 10

Test of Lowering Blood Pressure

1. Materials and Methods

1) Samples and solution: samples from Test Samples 1-6 and Control Samples 1-3 were labeled as S1, S2, S3, S4, S5, S6, and D1, D2, D3, respectively; 0.9% NaCl injection (physiological saline), pack size: 250 mL/bottle, Sichuan Kelun Pharmaceutical Co. Ltd., lot#: C13102005-1; distilled water, and picric acid, etc.

2) Instruments: DKB-501A High Precision Water Bath (Shanghai Senxin Laboratory Apparatus Ltd.); electronic constant temperature drying cabinet (Changsha Medical Devices Ltd.); PowerLab/4SP ML125 non-invasive blood pressure measurement system (ML125/R NIBP, MLT1199 Disposable BP Transducer/Cable Kit; ADInstruments Ltd., Australia); MP120-1 electronic balance (Shanghai Number Two Balance Instrument Factory).

3) Experimental animals: SHR rats (SPF level), weight 190-230 g, male, provided by Beijing Vital River Laboratory Animal Technology Co. Ltd., Certificate#: SCXK(Beijing) 2012-0001. Animals were raised in SPF level barrier level animal room, animal use license#: SYXK(Guangdong) 2012-0081. WISTAR male rats (SPF level) were provided by Beijing Vital River Laboratory Animal Technology Co. Ltd., Certificate#: SCXK(Beijing) 2012-0001.

4) Dosage setting: expected dosage for human adults is 3.0 g/60 kg·BW·day. Dosage used for rats was 10 times that of human. The dosage was calculated using raw drug amount.

5) Statistic analysis: data were processed using SPSS 17.0 statistical tool, parameters were displayed as mean±standard deviation (i+S), ANOVA test was used for comparison among groups, p<0.05 was defined as statistically significant.

2. Methods and Results 9-10 week old male spontaneously hypertensive rats (SHR) were randomly separated into 10 groups, 10 rats per group, named as hypertension model control group (administered with distilled water), S1 group, S2 group, S3 group, S4 group, S5 group, S6 group, D1 group, D2 group, and D3 group. 10 normal WISTAR rats were selected as normal control group (administered with distilled water). Animals in each group were intragastrically administered with different dosages of drugs, once per day, for a period of 4 W. Rat caudal artery blood pressure (systolic arterial pressure, SAP, mmHg) was measured using non-invasive caudal artery blood pressure measurement system, both before and after 4 W treatment.

Non-invasive tail cuff method (NIBP): a rat was placed into the rat fixer, allowing its tail exposed. Infrared heater was set to be 38° C. Rat tail was heated under radiation for about 10 mins until the tail becoming soft and caudal artery expanding sufficiently. Pressured tail cuff was passed through the rat tail and fixed at the tail root, so that rat caudal artery was in tight contact with the pulse sensor of the PowerLab ML125/R non-invasive caudal artery blood pressure measurement system. The pulse waveform was monitored, and blood pressure could be measured when stable pulse wave appeared. When the animal calmed down, pressure was increased in the tail cuff at 90-420 BPM (rat pressure increasing level), pulse wave could be seen to gradually diminish until disappear, then gas was gradually released in the tail cuff, pressure gradually decreased in the tail cuff, and pulse wave reappeared when the pressure reached SAP, the blood pressure of which was defined as the rat tail SAP. The measurement was repeated for 3 times, and average value was obtained. The pressure drop value (blood pressure drop value) was calculated as SAP after treatment minus SAP before treatment. The result is shown in Table 8.

TABLE 8

The effect of drug samples on blood pressure (SAP, mmHg) of SHR rats ($\bar{x} \pm S$)

| Group | n | Blood pressure before treatment (SAP, mmHg) | Blood pressure after 4 W treatment (SAP, mmHg) |
|---|---|---|---|
| Normal control group | 10 | 103.85 ± 13.62 | 108.24 ± 15.16 |
| Model control group | 10 | 178.66 ± 15.20# | 188.90 ± 15.19# |
| S1 group | 10 | 177.57 ± 15.65 | 170.86 ± 15.90* |
| S2 group | 10 | 176.93 ± 14.72 | 171.89 ± 14.15* |
| S3 group | 10 | 179.08 ± 12.98 | 169.94 ± 15.07* |
| S4 group | 10 | 177.35 ± 13.91 | 172.03 ± 16.42* |
| S5 group | 10 | 178.94 ± 12.99 | 171.44 ± 15.68* |
| S6 group | 10 | 178.03 ± 14.63 | 170.68 ± 15.13* |
| D1 group | 10 | 179.59 ± 15.02 | 174.08 ± 13.28* |
| D2 group | 10 | 178.11 ± 14.27 | 183.50 ± 15.69 |
| D3 group | 10 | 178.35 ± 14.86 | 181.46 ± 14.99 |

Note:
compared to normal control group: #p < 0.01;
compared to model control group: *p < 0.05.

The result showed that, rats in the model control group had significantly elevated blood pressure compared to that of rats in the normal control group, indicating spontaneously hypertensive rats as successful models. And, drugs of S1-S6 groups and D1 group significantly lowered the blood pressure of SHR rats after 4 W treatment (p<0.05), compared to model control group.

3. Conclusion

S1-S6 and D1 samples showed significant effects in lowering blood pressure, and the compositions of S1-S6 exhibited synergistic or enhanced effects in lowering blood pressure.

Example 11

In Vivo Efficacy Determination

Animal subjects or human subjects are assigned randomly into a control group and a treatment group. The treatment group is provided a therapeutically effective amount of the herbal extract composition, the gel capsule, the nutritional composition, or the pharmaceutical composition comprising (including consisting essentially of or consisting of) an extract of the herb combinations (e.g., *Cyclocarya paliurus* leaves, *Mori Cortex, Dendrobii Caulis* and *Citri Reticulatae Pericarpium*), with a predetermined dosage regimen over a predetermined period of time. The control group is provided with a placebo with the same dosage regimen and treatment duration. Blood glucose levels in all subjects of both experimental groups are monitored prior to the experiment, during the course of the experiment, and at the end of the experiment. Standard blood glucose kits, such as those relying on the nonspecific reducing property of glucose, and those using glucose specific enzymes, are used to monitor the blood glucose levels of the subjects. Statistical analysis is performed to compare the blood glucose levels at various time points in the course of the experiment between the control group and the treatment group, which is used along with other relevant data to determine the efficacy of the methods of treatment disclosed in the present invention.

What is claimed is:

1. A health care composition comprising about 30-40% (w) *Cyclocarya paliurus* leaves, about 30-40% (w) *Mori Cortex*, about 10-30% (w) *Dendrobii Caulis* and about 5-15% (w) *Citri Reticulatae Pericarpium*.

2. A method for preparing an herbal extract composition comprising an extract of *Cyclocarya paliurus* leaves, *Mori Cortex, Dendrobii Caulis* and *Citri Reticulatae Pericarpium*, the method comprising:

i) providing a mixture of *Cyclocarya paliurus* leaves, *Mori Cortex, Dendrobii Caulis* and *Citri Reticulatae Pericarpium*, wherein the mixture comprises about 30-40% (w) *Cyclocarya paliurus* leaves, about 30-40% (w) *Mori Cortex*, about 10-30% (w) *Dendrobii Caulis* and about 5-15% (w) *Citri Reticulatae Pericarpium*;

ii) extracting said mixture with water to obtain an aqueous extract;

iii) concentrating the aqueous extract to obtain a concentrated mixture;

iv) obtaining a liquid portion of said concentrated mixture; and v) drying said extract to produce an herbal extract composition.

3. An herbal extract composition prepared by a method according to claim 2.

4. A method for preparing a gel capsule comprising an herbal extract composition comprising an extract of *Cyclo-*

*carya paliurus* leaves, *Mori Cortex*, *Dendrobii Caulis* and *Citri Reticulatae Pericarpium*, a microcrystalline cellulose and calcium hydrogen phosphate, said method comprising:
   i) providing the herbal extract composition, wherein the herbal extract composition comprises about 30-40% (w) *Cyclocarya paliurus* leaves, about 30-40% (w) *Mori Cortex*, about 10-30% (w) *Dendrobii Caulis* and about 5-15% (w) *Citri Reticulatae Pericarpium*;
   ii) mixing said herbal extract composition with a microcrystalline cellulose and calcium hydrogen phosphate to obtain a first mixture;
   iii) treating a portion of said first mixture with an alcoholic solvent to obtain a wet granule;
   iv) drying the wet granule to obtain a dry granule;
   v) mixing said dry granule with magnesium stearate to obtain a second mixture; and
   vi) filling a portion of said second mixture in a gel capsule.

5. A gel capsule prepared by the method according to claim 4.

6. A method for treating a disease or condition responsive to lowering of blood sugar in a subject in need thereof comprising administering to the subject a therapeutically effective amount of the health care composition of claim 1.

7. A method of treating hyperglycemia and/or hyperlipidemia in a subject in need thereof comprising administering to the subject a therapeutically effective amount of the health care composition of claim 1.

8. A method for treating a disease or condition responsive to lowering of blood sugar in a subject in need thereof comprising administering to the subject a therapeutically effective amount of the herbal extract composition of claim 3.

9. A method for treating a disease or condition responsive to lowering of blood sugar in a subject in need thereof comprising administering to the subject a therapeutically effective amount of the gel capsule of claim 5.

10. A method of treating hyperglycemia and/or hyperlipidemia in a subject in need thereof comprising administering to the subject a therapeutically effective amount of the herbal extract composition of claim 3.

11. A method of treating hyperglycemia and/or hyperlipidemia in a subject in need thereof comprising administering to the subject a therapeutically effective amount of the gel capsule of claim 5.

12. The method of claim 4, wherein the herbal extract composition comprises about 35% (w) *Cyclocarya paliurus* leaves, about 35% (w) *Mori Cortex*, about 20% (w) *Dendrobii Caulis* and about 10% (w) *Citri Reticulatae Pericarpium*.

13. A gel capsule prepared by the method according to claim 12.

14. The health care composition of claim 1, wherein the health care composition comprises about 35% (w) *Cyclocarya paliurus* leaves, about 35% (w) *Mori Cortex*, about 20% (w) *Dendrobii Caulis* and about 10% (w) *Citri Reticulatae Pericarpium*.

15. The method of claim 2, wherein the mixture comprises about 35% (w) *Cyclocarya paliurus* leaves, about 35% (w) *Mori Cortex*, about 20% (w) *Dendrobii Caulis* and about 10% (w) *Citri Reticulatae Pericarpium*.

16. A method for treating a disease or condition responsive to lowering of blood sugar in a subject in need thereof comprising administering to the subject a therapeutically effective amount of the health care composition of claim 14.

17. A method of treating hyperglycemia and/or hyperlipidemia in a subject in need thereof comprising administering to the subject a therapeutically effective amount of the health care composition of claim 14.

\* \* \* \* \*